(12) United States Patent
Beckley

(10) Patent No.: US 11,061,026 B2
(45) Date of Patent: *Jul. 13, 2021

(54) SYSTEM OF EVALUATING CORPUS LUTEUM FUNCTION BY RECURRENTLY EVALUATING PROGESTERONE NON-SERUM BODILY FLUIDS ON MULTIPLE DAYS

(71) Applicant: MFB Fertility, Inc., Erie, CO (US)

(72) Inventor: Amy Beckley, Erie, CO (US)

(73) Assignee: MFB Fertility, Inc., Erie, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/732,823

(22) Filed: Jan. 2, 2020

(65) Prior Publication Data

US 2020/0141954 A1 May 7, 2020

Related U.S. Application Data

(63) Continuation-in-part of application No. 16/544,554, filed on Aug. 19, 2019, and a continuation-in-part of
(Continued)

(51) Int. Cl.
*G01N 33/558* (2006.01)
*G01N 33/74* (2006.01)
(Continued)

(52) U.S. Cl.
CPC ....... *G01N 33/558* (2013.01); *G01N 21/6428* (2013.01); *G01N 33/689* (2013.01); *G01N 33/743* (2013.01); *G01N 33/76* (2013.01)

(58) Field of Classification Search
CPC ............ G01N 21/6428; G01N 33/689; G01N 33/743; G01N 33/558; G01N 33/76; G01N 2800/368; B01L 2300/0825
See application file for complete search history.

(56) References Cited

U.S. PATENT DOCUMENTS 4,376,110 A * 3/1983 David ................ G01N 33/58
435/5
4,450,239 A 5/1984 Chatterton
(Continued)

FOREIGN PATENT DOCUMENTS

CN 104697938 B 4/2018
EP 0656118 B1 6/1995
(Continued)

OTHER PUBLICATIONS

Pauillac et al, "An improved method for the production of antibodies to lipophilic carboxylic hapten using small amount of hapten-carrier conjugate", Journal of Immunological Methods, 220, 1998, 105-114 (Year: 1998).*
(Continued)

*Primary Examiner* — Christopher L Chin
(74) *Attorney, Agent, or Firm* — Hall Estill Attorneys at Law; Jeffrey R. Schell

(57) ABSTRACT

Disclosed herein are devices, systems, methods and kits for performing immunoassay tests to detect for at least progesterone or analytes of progesterone on a sample in association with diagnosing problems and issues associated with corpus luteum functionality. The immunoassay devices and methods may be used in conjunction with diagnostic reader systems and/or a base unit for obtaining a sensitive read-out of the immunoassay results. The immunoassay devices and methods may utilize a competitive binding-like assay and a sandwich binding assay to detect at least progesterone or analytes of progesterone in a sample.

5 Claims, 5 Drawing Sheets

Related U.S. Application Data application No. 15/974,229, filed on May 8, 2018, and a continuation-in-part of application No. 15/900,794, filed on Feb. 20, 2018, now abandoned, application No. 16/732,823, filed on Jan. 2, 2020, which is a continuation-in-part of application No. 16/381,229, filed as application No. PCT/US2018/068027 on Dec. 28, 2018.

(60) Provisional application No. 62/720,953, filed on Aug. 22, 2018, provisional application No. 62/503,223, filed on May 8, 2017, provisional application No. 62/460,307, filed on Feb. 17, 2017, provisional application No. 62/611,467, filed on Dec. 28, 2017.

(51) Int. Cl.
  *G01N 21/64* (2006.01)
  *G01N 33/68* (2006.01)
  *G01N 33/76* (2006.01)

(56) References Cited

U.S. PATENT DOCUMENTS

| | | | | |
|---|---|---|---|---|
| 5,158,869 | A * | 10/1992 | Pouletty | G01N 33/54366 422/401 |
| 6,924,153 | B1 * | 8/2005 | Boehringer | G01N 33/558 422/420 |
| 7,943,395 | B2 * | 5/2011 | Wei | G01N 33/558 436/514 |
| 9,386,221 | B2 | 7/2016 | Kauniskangas et al. | |
| 9,787,815 | B2 | 10/2017 | Erickson et al. | |
| 2006/0121626 | A1 | 6/2006 | Imrich | |
| 2010/0312137 | A1 | 12/2010 | Gilmour et al. | |
| 2013/0273563 | A1 | 10/2013 | Ehrenkranz | |
| 2015/0094227 | A1 * | 4/2015 | McCarthy | G01N 33/743 506/9 |
| 2015/0304555 | A1 | 10/2015 | Ehrenkranz | |
| 2015/0338387 | A1 | 11/2015 | Ehrenkranz | |
| 2016/0139156 | A1 | 5/2016 | Lakdawala | |
| 2016/0167042 | A1 | 6/2016 | Tyrrell et al. | |
| 2016/0178607 | A1 | 6/2016 | Husheer et al. | |
| 2017/0007215 | A1 | 1/2017 | Podoly | |
| 2017/0011194 | A1 | 1/2017 | Arshad et al. | |
| 2018/0088136 | A1 * | 3/2018 | Saji | G01N 33/743 |
| 2018/0321251 | A1 | 11/2018 | Beckley | |
| 2020/0141954 | A1 | 5/2020 | Beckley | |

FOREIGN PATENT DOCUMENTS

| | | |
|---|---|---|
| EP | 2788764 A1 | 10/2014 |
| EP | 2839264 A1 | 2/2015 |
| EP | 2861991 A1 | 4/2015 |
| EP | 3052944 A1 | 8/2016 |
| WO | 1995016920 A1 | 6/1995 |
| WO | 9839657 A1 | 9/1998 |
| WO | 2007/049157 A2 | 5/2007 |
| WO | 2016/115608 A1 | 7/2016 |
| WO | 2016/166415 A1 | 10/2016 |
| WO | 2017/058827 A1 | 4/2017 |
| WO | 2017/180909 A1 | 10/2017 |

OTHER PUBLICATIONS

Vyjayanthi et al, "Binding characteristics of bovine serum albumin-afloxin B1 to polystyrene microtiter plates: Importance of hapten to carrier protein molar ratio", Indian Journal of Experimental Biology, vol. 33, May 1995, 329-332 (Year: 1995).*

Hermanson, G.T., "Bioconjugate Techniques", Academic Press, San Diego, 1996, p. 878 (Year: 1996).*

Maggio, "Enzyme Immunoassay", CRC Press 1980, 54-70.*

Mesen, T.B., et al., "Progesterone and the Luteal Phase: A Requisite to Reproduction," Obstetrics and Gynecology Clinics of North America, Mar. 2015, vol. 42, No. 1, pp. 135-151; p. 3, 4th paragraph; p. 4, 3rd paragraph; p. 6, 5th paragraph; p. 7, 2nd paragraph; p. 9, 2nd paragraph; DOI: 10.1016/j.ogc.2014.10.003.

MFB Fertility Inc., "How do Ovulation Double Check Tests Work," Oct. 2, 2017 [retrieved on Feb. 25, 2019]. Retrieved from the internet; timestamps 0:07-0:45, 1:00-2:30.

Munro, C.J., et al., "Relationship of Serum Estradiol and Progesterone Concentrations to the Excretion Profiles of Their Major Urinary Metabolites as Measured by Enzyme Immunoassay and Radioimmunoassay," Clinical Chemistry, Jun. 1991, vol. 37, No. 6, pp. 838-844; p. 840, 2nd column, 3rd paragraph; Table 2.

PCT International Search Report with attached Written Opinion of the International Searching Authority for International Application No. PCT/US18/68027, dated Mar. 26, 2019, 16 pages.

GooglePlay, "DaysyView" Valley Electronics, Aug. 20, 2015, p. 1, Paragraphs 1 and 3 (5 pages).

PCT International Search Report with attached Written Opinion of the International Searching Authority for International Application No. PCT/US20/40600, dated Nov. 20, 2020, 13 pages.

\* cited by examiner

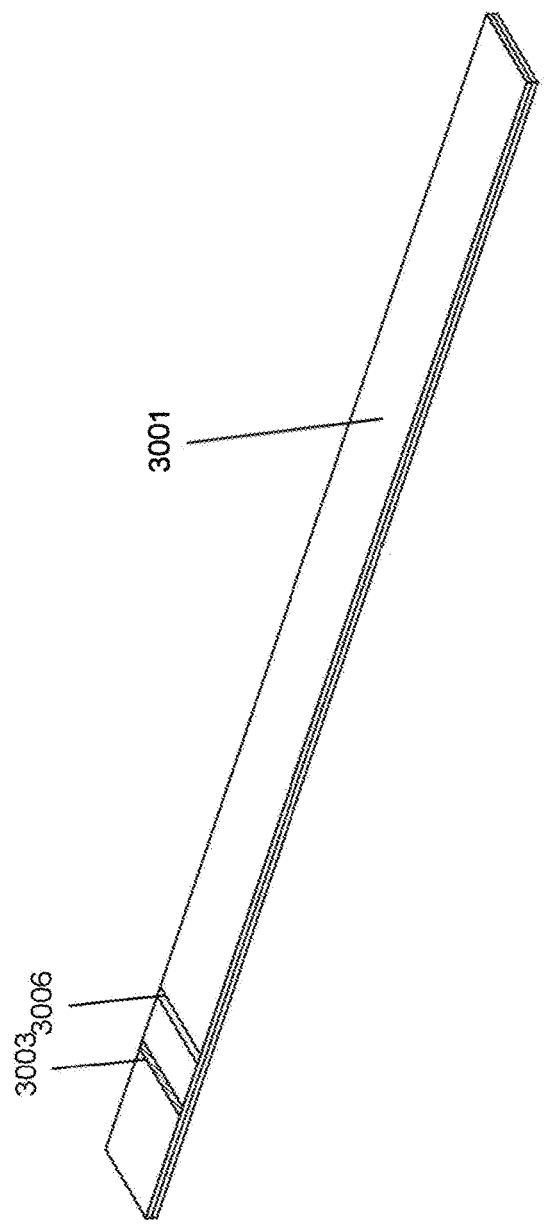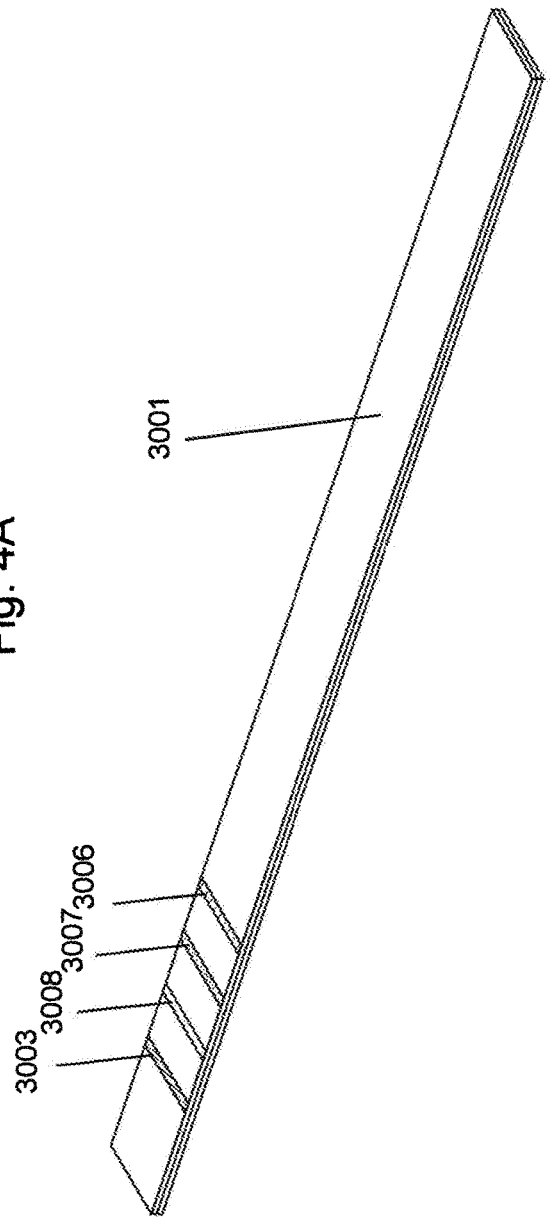

SYSTEM OF EVALUATING CORPUS LUTEUM FUNCTION BY RECURRENTLY EVALUATING PROGESTERONE NON-SERUM BODILY FLUIDS ON MULTIPLE DAYS

CROSS-REFERENCE TO RELATED APPLICATIONS

This application is a continuation-in-part application of U.S. Non-provisional patent application Ser. No. 16/544,554, filed on Aug. 19, 2019, which is a conversion of U.S. Provisional Patent Application No. 62/720,953, filed on Aug. 22, 2018, the entire contents of said applications are hereby incorporated by reference. This application is also a continuation-in-part of U.S. Non-provisional patent application Ser. No. 15/974,229 filed May 8, 2018, which is a conversion of U.S. Provisional Application No. 62/503,223 filed May 8, 2017; and U.S. Non-provisional patent application Ser. No. 15/900,794, filed Feb. 20, 2018, which is a conversion of U.S. Provisional Application No. 62/460,307 filed Feb. 17, 2017, the entire contents of said applications are hereby incorporated by reference. This application is also a continuation-in-part of U.S. Non-provisional patent application Ser. No. 16/381,229 filed Apr. 11, 2019, which is a national stage application of PCT Application No. PCT/US18/68027, filed Dec. 28, 2018, which is a PCT application claiming priority to U.S. Provisional Application No. 62/611,467 filed Dec. 28, 2017, the entire contents of said applications are hereby incorporated by reference.

FIELD OF THE INVENTION

The present invention relates to the field of hormone diagnostics. More specifically, the present invention relates to urine based lateral flow assays for the detection of hormones relevant to the corpus luteum and methods of interpretation and digital quantification thereof.

BACKGROUND OF THE INVENTION

The Corpus Luteum is a mass of cells that forms in an ovary. During ovulation, an egg is released from a dominant follicle. Following the release of the egg and subsequent fertilization, the follicle seals itself off and forms the Corpus Luteum. The Corpus Luteum produces the hormone progesterone during the luteal phase and during early pregnancy. The luteal phase is the part of the menstrual cycle that occurs after ovulation. It typically lasts 12-16 days, during time which the Corpus Luteum functions. Following conception, the Corpus Luteum functions to produce progesterone until the placenta can produce adequate levels to sustain the pregnancy, which usually occurs between 7 and 9 weeks of pregnancy. Progesterone is essential during early pregnancy because it allows the uterus to grow without having contractions, stabilizes the lining of the uterus, and improves blood flow and oxygen supply.

The Corpus Luteum a key anatomical structure associated with menstrual cycle timing. Women often attempt to chart their menstrual cycles with the aid of home use urine or saliva tests configured to detect Luteinizing Hormone (LH). However, the presence of LH only predicts the onset of ovulation and only indicates one portion of the menstrual cycle. The presence of LH does not confirm that the Corpus Luteum is functioning properly to actually release an egg. Only the corresponding release of progesterone beyond a threshold level indicates that an egg has been released. It would therefore be desirable to have an efficient and accurate method to track progesterone non-invasively and without delays associated with third party review of testing results to better understand menstrual cycle timing and Corpus Luteum functionality.

To accurately chart an entire menstrual cycle, a woman must understand the ovulation date as indicated by strips that detect for the presence of lutenizing hormone, counting days from the date of beginning menstruation, or measuring basal body temperature, for instance. Therefore, a progesterone test that does not deliver results on the same day of the test (i.e. a test that requires delivery of a sample to a lab) is not practical to allow a woman to utilize a method to measure and track her progesterone on a daily basis. The excessive waiting for the results of such lab-based progesterone tests, in addition to multiplying anxiety, prevent accurate tracking because the time that it takes to deliver results presents a picture of what occurred in a past part of the menstrual cycle, not a current part of the menstrual cycle. Thus, the use of progesterone testing that requires multiple days for results does not allow for accurate mapping of the cycle until such time that the information loses its value. It would therefore be desirable to have a method that incorporates immediate progesterone testing and tracking to effectively chart a menstrual cycle, determine at which point the subject is in the menstrual cycle, immediately utilize the results and begin the appropriate corrective protocols as necessary.

The Corpus Luteum is supported and maintained by lutenizing hormone (LH) initially, and then the pregnancy hormone human chorionic gonadotrophin (HCG). The corpus luteum begins to decrease in size at around 7-9 weeks of pregnancy. When fertilization or implantation do not occur, the Corpus Luteum will begin to break down 10-14 days following ovulation. This causes a decline in estrogen and progesterone levels, leading to the start of another menstrual period.

Corpus Luteum problems often result from the insufficient production of progesterone or if progesterone production ends too soon. If progesterone is absent or levels are too low, irregular and heavy menstrual bleeding can occur. Lack of progesterone in the bloodstream can mean the ovary has failed to release an egg at ovulation, as can occur in women with polycystic ovary syndrome.

The evaluation of Corpus Luteum functionality is important in association with diagnosing and preventing fertility-related problems. A drop in progesterone during pregnancy can result in a miscarriage and early labor. However, there are available treatments to address related conditions. For instance, those at risk of giving birth too soon can be given a synthetic form of progesterone to delay the onset of labor. Therefore, it would be desirable to have a method that allows for the instantaneous review of results showing progesterone above or below a threshold level over a period of days incorporating a specifically configured device that allows for the delivery of immediate or near-immediate results on each day to alert a pregnant woman immediately that a miscarriage may be imminent without progesterone supplementation.

Corpus Luteum function can also be evaluated by an accurate measurement of progesterone. As a temporary endocrine gland that the female body produces after ovulation during the second half of the menstrual cycle, the Corpus Luteum secretes progesterone, impacting the blood progesterone level. For a woman who menstruates, her blood progesterone level should be low at the beginning of each menstrual cycle. It should peak several days after she has ovulated properly. Then it should fall back to low levels, unless the woman has become pregnant in which case progesterone will continue to be secreted to prevent uterine contractions that may disturb the growing embryo. Ranges of these levels remain generally consistent among properly ovulating females of a particular population, therefore evaluation of these levels to determine whether the test results correlate with the expected progesterone range of a particular population can be used to either confirm proper Corpus Luteum functioning, among other valuable information. However, such results have been only generally available via a blood test or mail-in kit, which limits the availability of repetitive testing over a period of several subsequent days.

The primary present mechanism for evaluating the production of progesterone in woman's body is via a serum progesterone test, or blood test. During such procedure, a medical professional collects a sample of the patient's blood in their office or sends the patient to another site to have blood drawn. Typically the test is then sent to an external lab for testing, a process that typically requires several days to complete. Serum progesterone levels are typically measured in nanograms per milliliter (ng/mL) in the United States of America. Once results are generated from the laboratory, the laboratory will send them to the patient's medical professional, who will generally relay them back to the patient. Many inconveniences to the patient arise from prior art methods of evaluating progesterone via serum draws on a recurrent basis. For many patients, particularly patients living in rural areas, access to blood labs requires a significant expenditure in time and travel costs. Also, for many patients, a visit to a blood testing facility requires missed work. For all patients, the pain and invasive nature of blood testing represents an area for which inventive improvement is desirable. However, more specifically for serum progesterone testing and any other progesterone test that generally requires more than one day for sample collection and evaluation, collection of results on subsequent days without near-instantaneous results for each sample evaluation is impractical for the purposes of accurate corpus luteum evaluation. The slow nature of receiving such test results makes it impractical for evaluation of corpus luteum function that can usefully be applied by the subject for diagnosis and corrective efforts on a continuous basis. Therefore, it would be desirable to have a method for testing for corpus luteum functionality where results may efficiently be collected on subsequent days to correct the drawbacks of previously utilized technologies by utilizing a technology that allows for aggregation and evaluation of progesterone testing results on a near-instantaneous basis in subsequent days.

A variety of devices and methods exist that incorporate a base unit configured to evaluate urine for the presence or absence of one or more hormones and/or analytes in a bodily fluid. Examples of such devices and methods are further described in International Patent Application PCT/CN2017/095452 filed on Aug. 1, 2017, in International Publication Number WO 2019/023926 A1, and U.S. patent application Ser. No. 16/302,085, filed on Jul. 11, 2019, each of which is hereby incorporated by reference herein in its entirety. While such devices and methods have worked in a variety of contexts, such devices lack the specific configuration necessary to detect the presence or absence of critical hormones and analytes associated with the menstrual cycle. Moreover, such items lack the associated steps necessary to detect and address issues associated with corpus luteum functionality.

More specifically, the prior art lacks the specific configuration to enable a test that evaluates urine for the presence of progesterone or progesterone analytes beyond a threshold and at timeframes relevant to assess corpus luteum functionality. It remains desirable to provide an improved system and method to a user to gain near-instantaneous results for the presence or absence of progesterone or its analytes by evaluation of urine or saliva on a daily basis without visitation to a clinic. Such a specifically configured test for urine has not been available until the recent development of the Proov rapid response urine progesterone test by MFB Fertility, Inc., the present applicant, elements of which are further described in PCT Patent Application PCT/US18/68027 and U.S. patent application Ser. No. 16/381,229, each of which are hereby incorporated by reference in their entirety. What also would be desirable is a saliva test configured to sample saliva and provide near-instantaneous results for the presence of progesterone at or above a level corresponding to proper Corpus Luteum functioning to a user as a non-urinary alternative, without requiring the user to deliver the results to a lab for interpretation.

Moreover, existing methods often require direction by a physician for evaluation. Typically, a woman suffering from infertility would seek guidance from a physician. In many cases however, physicians either choose against treating or are prohibited by insurance companies from providing treatment until the patient can document that she has tried for more than twelve months to conceive. When the physician provides treatment, often the first evaluation involves determining whether there is a blocked tube, sperm deficiency, anatomical structural abnormality, or genetic factors prior to evaluating hormonal problems more generally associated with Corpus Luteum functionality. Each of these issues requires time to evaluate. Due to the biological clock, women often at best suffer anxiety as the diagnostic process progresses, and at worst move from a phase in their lives where they can conceive and maintain pregnancy to a phase where they cannot. Thus, it remains desirable for an alternative method to empower women to more rapidly and independently understand and diagnose potential Corpus Luteum functionality problems without the need for involving a physician.

A variety of other problems result from improper Corpus Luteum functioning. For instance, improper luteal function is linked to mood changes and depression. Improper luteal function has also been linked to weight gain, brittle bones, memory loss, PMS, anxiety, perimenopause, and increased risk of ovarian and breast cancer. It would therefore be desirable to have an efficient method to detect improper Corpus Luteum functioning following or preceding the onset of such maladies to allocate appropriate treatment resources.

BRIEF SUMMARY OF THE INVENTION

The present inventor has developed a system incorporating a specially configured test device useful in association with evaluating corpus luteum functioning. The present inventor has relatedly developed methods in association with the usage of such system for evaluating a non-serum bodily fluid daily over a period of multiple days for the presence of progesterone or an analyte of progesterone beyond a threshold to detect for suboptimal corpus luteum functioning.

BRIEF DESCRIPTION OF THE SEVERAL VIEWS OF THE FIGURES

FIG. 4A depicts an embodiment of the test strip featuring a control line and a test line to detect for the presence or absence of PdG.

FIG. 4B depicts an embodiment of the test strip featuring a control line and a plurality of test lines, one of said test lines configured to detect for the presence or absence of PdG.

DETAILED DESCRIPTION OF THE INVENTION

Figure 1:
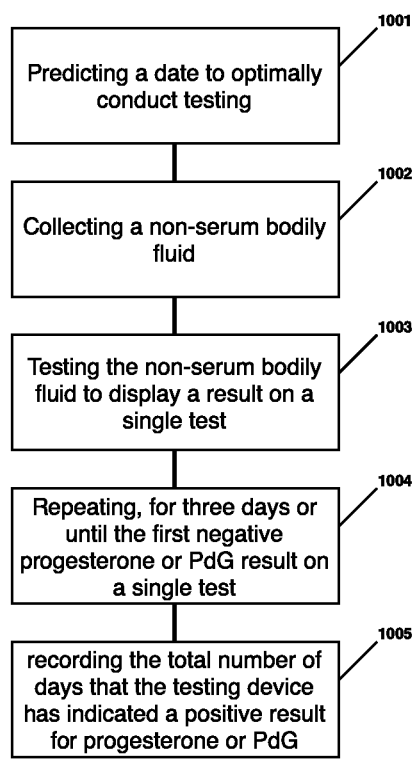
FIG. 1 shows method steps associated with a method to evaluate corpus luteum functionality.

The present inventor has developed a system for evaluation of corpus luteum functionality. In an embodiment, the system incorporates a specially configured device for evaluating a non-serum bodily fluid daily over a period of multiple days for the presence of at least progesterone or an analyte of progesterone beyond a threshold to detect for suboptimal corpus luteum functioning. An embodiment of the system is designed to function in accordance with a method to evaluate a non-serum bodily fluid daily over a period of multiple days.

The method addresses the drawbacks of previous methods of corpus luteum evaluation which do not leverage the system or the specially configured devices contemplated for use within the context of the system. The present inventor has discovered a method addressing at least one specific drawback associated with blood serum testing for progesterone, useful in association with evaluating corpus luteum functionality, specifically that progesterone in the bloodstream is cyclical by nature. The cycle of serum progesterone happens as result the corpus luteum forming a part of the endocrine system. More specifically, the corpus luteum secretes progesterone in waves responding to changes in serum progesterone levels. Therefore, as the present inventor has recognized, a single point serum progesterone test may not accurately present an accurate representation of corpus luteum functionality, as it presents the progesterone level at only a single point of time, rather than reporting a trend of serum progesterone levels.

To address this shortcoming, the present inventor devised a system, which in an embodiment comprises specially configured single tests able to evaluate urine for the presence of at least progesterone or an analyte of progesterone (such as PdG), which may comprise one or more test strips 3001 configured to evaluate non-serum bodily fluids, such as those further described in U.S. patent application Ser. No. 16/544,554 filed on Aug. 19, 2019, which is incorporated by reference herein in its entirety. The present inventor has also recognized that the novel configuration of such single tests are well suited for utilization with additionally configured base units and processing devices to create additional functionality as described elsewhere herein.

In association with an embodiment of the system, a test strip 3001 configured to evaluate urine for the presence of at least progesterone or an analyte of progesterone (e.g., PdG) optionally is configured such that the first capture region is configured such that, when used with a base unit, a first optical signal (e.g., a fluorescent signal) is capable of being detected at the first capture region. The first optical signal may be a readout for the amount of progesterone analyte (e.g., PdG) in the sample, for example, by detecting the amount of first detection reagent bound to the first capture reagent. In such cases, the first optical signal increases when the amount of first analyte present in the sample is low, and the first optical signal decreases when the amount of first analyte present in the sample is high. The optical signal at the first capture region may be proportional to the amount of first analyte present in the sample. In various aspects, the capture zone further comprises a second capture region configured to produce an optical signal likewise corresponding to the presence or absence of a second analyte. In various aspects of the systems and methods herein, the test strip 3001 is configured for utilization in conjunction with a base unit 4001, optionally configured to evaluate a test strip 3001 contained within a cartridge 4002, together comprising a diagnostic test system.

In one aspect, a diagnostic test system is provided comprising: a housing, comprising: a) a port for receiving an assay device, said assay device comprising two or more capture regions; b) a reader comprising: i) one or more light sources for illuminating said two or more capture regions; ii) one or more light detectors for detecting optical signals from said two or more capture regions; and c) a data analyzer having one or more processors configured to: A) receive said optical signals; and determine an amount of at least a first analyte and a second analyte present in a biological sample based on said optical signals, wherein an optical signal of a first of said two or more capture regions increases with decreasing amounts of said first analyte present in said biological sample, and an optical signal of a second of said two or more capture regions increases with increasing amounts of said second analyte present in said biological sample; wherein in an embodiment at least one of the said first capture region or the said second capture regions is configured to detect PdG present in a biological sample in accord with at least the teachings of U.S. patent application Ser. No. 16/544,554 filed on Aug. 19, 2019, which is incorporated by reference herein in its entirety.

The diagnostic test system may include a housing for containing the components of the system. The housing can be constructed of any suitable material. The housing may be configured to receive an immunoassay device configured to detect for at least the presence or absence of progesterone or a progesterone analyte of the disclosure. For example, the housing may include a port or opening for receiving the immunoassay device configured to detect for at least the presence or absence of progesterone or a progesterone analyte. The system may further include, contained within the housing, a reader device. The reader device may include one or more light sources for illuminating the immunoassay device or a region of the immunoassay device configured to detect for at least the presence or absence of progesterone or a progesterone analyte. In one non-limiting example, the one or more light sources are configured to illuminate the capture zone of an immunoassay device configured to detect for at least the presence or absence of progesterone or a progesterone analyte of the disclosure. The type of light source suitable for use with the immunoassay devices will depend on the chemistry of the immunoassay device. In one particular example, the one or more light sources are used to illuminate a detectable label provided by the immunoassay device configured to detect for at least the presence or absence of progesterone or a progesterone analyte. In a particular example, the detectable label provided on the immunoassay device is a fluorophore, and therefore, the one or more light sources of the reader device should include a fluorescent light source (e.g., a light-emitting diode (LED)). It is to be understood that the wavelength of light provided by the light source of the reader device should be selected based on the excitation wavelength of the detectable label, and can readily be selected by a person of skill in the art.

The reader may be configured to illuminate the capture zone and/or the control zone of an immunoassay device configured to detect for at least the presence or absence of progesterone or a progesterone analyte (e.g. PdG) of the disclosure. For example, the reader may be configured to illuminate the first capture region configured to signal the presence or absence of progesterone or a progesterone analyte (e.g. PdG), the second capture region, the first control region, the second control region, or any combination thereof. In some cases, the reader is configured to scan across the test strip of an immunoassay device. In such cases where the immunoassay device utilizes a single fluorophore, the reader may contain a single fluorescent light source. In cases where the immunoassay device utilizes more than one fluorophore, the reader may contain more than one fluorescent light source.

The reader may further comprise one or more light detectors (e.g., a photodetector) for detecting optical signals from the immunoassay device. Generally speaking, the one or more light detectors should be capable of distinguishing between emitted light at a first discrete position and a second discrete position on the immunoassay device. This may be accomplished by, e.g., the one or more light sources scanning across the test strip of the immunoassay device and determining the position of the emitted light on the immunoassay device.

The diagnostic test device may further comprise a data analyzer. The data analyzer may have one or more processors configured to receive an optical signal. In some cases, the data analyzer is in operable communication with a reader device. The data analyzer may be configured to determine an amount of analytes present in a sample, for example, by measuring an amount of optical signal produced at the capture zone of an immunoassay device configured to detect for at least the presence or absence of progesterone or a progesterone analyte. For example, the data analyzer may be configured to calculate the area under the curve of a signal intensity plot. The data analyzer may further be configured to determine the differences between signal intensities among the multiple discrete regions on the test strip. For example, the data analyzer may be configured to determine the difference between the signal intensity at the first capture region and the signal intensity at the second control region. The data analyzer may further be configured to determine the difference between the signal intensity at the second capture region and the signal intensity at the first control region. The data analyzer may further be configured to calculate an amount or concentration of the analytes present in the sample, in one aspect at least one of the analytes present being an analyte of progesterone (e.g. PdG). The data analyzer may be further configured to detect a binary optical pattern. The binary optical pattern can be generated by two fluorescent materials which excitation and/or emission spectrum differs in wavelength. In some cases, the binary optical pattern can be generated by one fluorescent material and one light absorbent material. The detection reagents may be conjugated with the two types of materials respectively and can be captured in the same capture zone, such that the capture zone may generate two different optical signal patterns in the data analyzer.

Figure 5A:
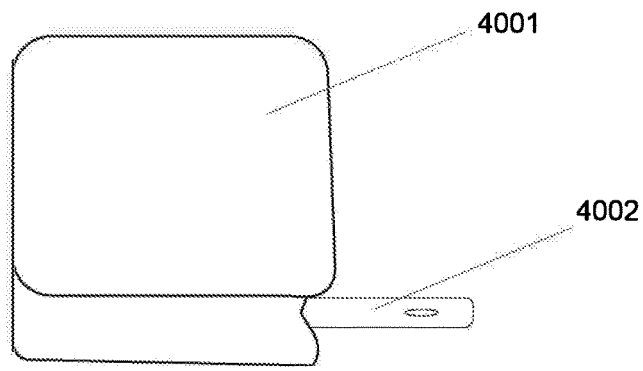
FIG. 5A depicts an embodiment of a base unit shown in an intended use in conjunction with a cartridge containing a test strip configured to evaluate a bodily fluid for the presence or absence of at least PdG.
Figure 5B:
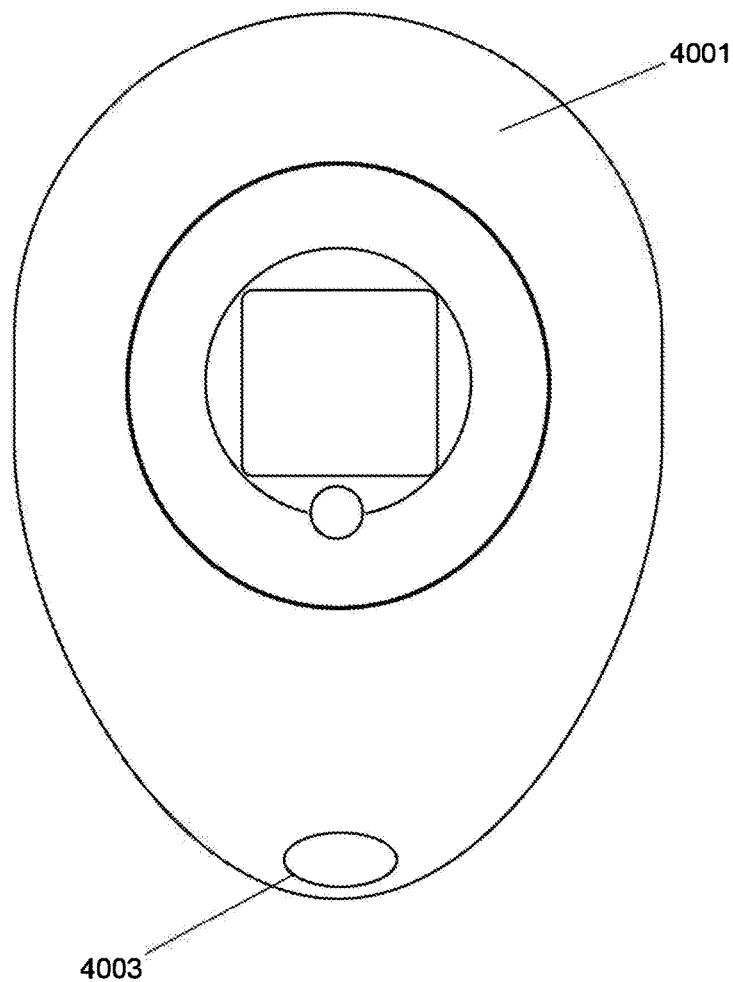
FIG. 5B depicts an alternative embodiment of a base unit shown in an intended use in conjunction with a cartridge containing a test strip configured to evaluate a bodily fluid for the presence or absence of at least PdG.
Figure 6:
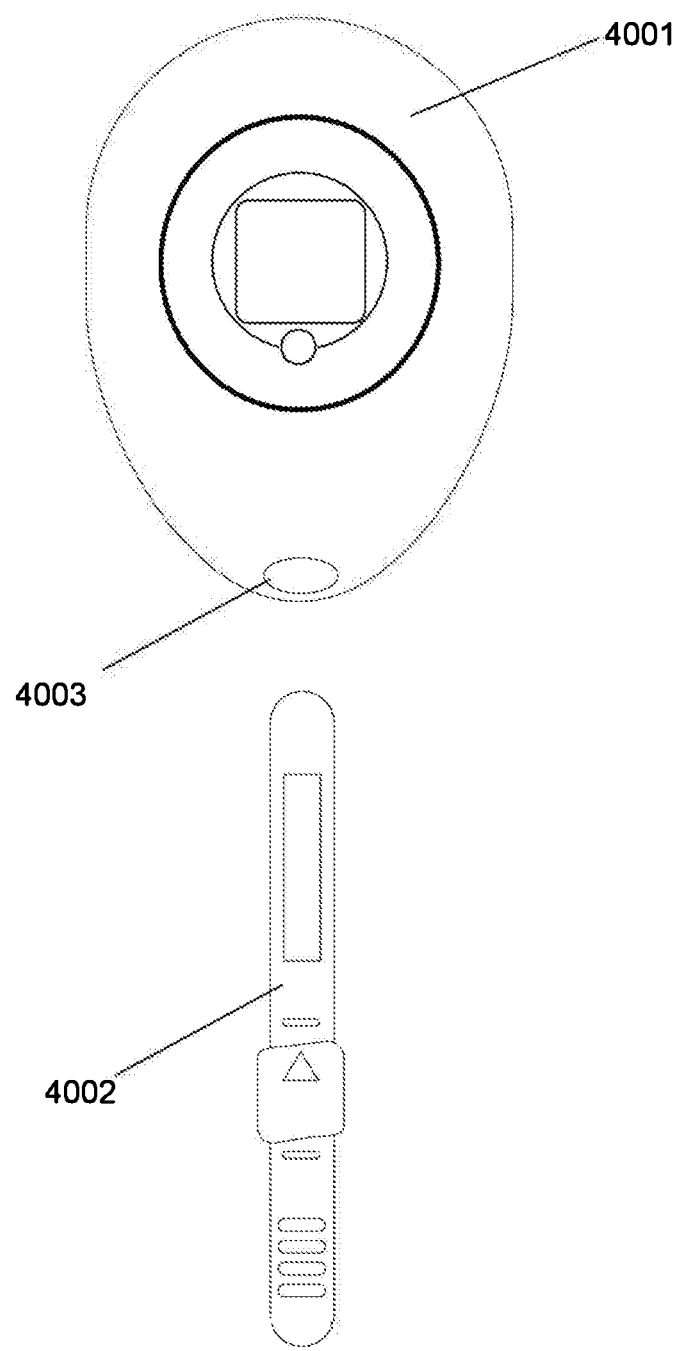
FIG. 6 depicts and embodiment of a test strip contained within a cartridge in exemplary use in association with a base unit.

In various aspects, the system may comprise a housing for containing the electronic components of the system such as that shown in FIGS. 5A, 5B and 6. The system may have a top housing and a bottom housing. The top housing may comprise a display module for displaying the results of an immunoassay configured to detect for at least the presence or absence of progesterone or a progesterone analyte as described herein. The system may further comprise a display cover. The system may further comprise a battery. The system may further comprise an optomechanics module. The optomechanics module may comprise the one or more light sources and one or more light detectors as described above. The system may further comprise a circuit board containing electronic components. The cassette or housing of the immunoassay test device configured to detect for at least the presence or absence of progesterone or a progesterone analyte may include a cavity. The chamber or receiving port of the diagnostic test system may include a ball bearing contained within the inner wall of the chamber. The ball bearing may hook or latch into the cavity of the test device, thereby locking the immunoassay test device configured to detect for at least the presence or absence of progesterone or a progesterone analyte into the receiving chamber of the diagnostic test system.

The diagnostic test system may include an optomechanics module comprising the one or more light sources for illuminating the test strip of the immunoassay device configured to detect for at least the presence or absence of progesterone or a progesterone analyte. The optomechanics module may be movable across an optical axis such that the optomechanics module moves laterally across the test strip of the immunoassay device configured to detect for at least the presence or absence of progesterone or a progesterone analyte, thereby scanning the test strip. The diagnostic test system may further comprise an actuation module. The actuation module may comprise one or more motors configured to actuate/move the optomechanics module. In some embodiments, the motors may be coupled to a rack and pinion mechanism that is configured to translate the optomechanics module along one or more directions. For example, the optomechanics module can be translated along a longitudinal axis of the test strip of the immunoassay device configured to detect for at least the presence or absence of progesterone or a progesterone analyte. The direction(s) of translation may or may not be orthogonal to an optical axis of the optomechanics module. The direction(s) of translation may be parallel to the longitudinal axis of the test strip, and the optical axis may be orthogonal to the longitudinal axis or a planar surface of the test strip. In some cases, the direction(s) of translation need not be parallel to the longitudinal axis of the test strip, and the optical axis need not be orthogonal to the longitudinal axis (or a planar surface) of the test strip. For example, the direction(s) of translation and/or the optical axis may be at an oblique angle relative to the longitudinal axis of the test strip.

In various aspects, the diagnostic test system may include an optical configuration suitable for use with the diagnostic test system and positioning of the optics above a test strip of an immunoassay device configured to detect for at least the presence or absence of progesterone or a progesterone analyte. The optical configuration may include a light source (e.g., a light-emitting diode (LED) for illuminating the test strip. The optical configuration may further include one or more lens, a filter, optical beamsplitters, or any combination thereof. The optical configuration may further include a photodetector for detecting an optical signal from the immunoassay device configured to detect for at least the presence of progesterone or a progesterone analyte. In an example, the system is configured to an excitation/emission spectra with an excitation wavelength of 492 nm and an emission wavelength of 512 nm.

In some cases, the diagnostic test device generates measurement results (e.g., concentration or relative amounts of analytes present in the sample) from a completed assay performed on the test device, as described throughout. In some cases, the diagnostic test device displays the measurement results on a screen contained within the device. Data containing the measurement results can be transmitted from the diagnostic test device to a mobile device and/or to a server. The data may be transmitted via one or more wireless or wired communication channels. The wireless communication channels may comprise Bluetooth®, WiFi, 3G, and/or 4G networks. The data containing the measurement results may be stored in a memory on the diagnostic test device when the diagnostic test device is not in operable communication with the mobile device and/or the server. The data may be transmitted from the diagnostic test device to the mobile device and/or the server when operable communication between the diagnostic test device and the mobile device and/or the server is re-established.

Further provided herein, in one aspect for inclusion within the context of a system for evaluating corpus luteum functionality, are kits which may include any number of immunoassay test devices configured to detect for at least the presence of progesterone or a progesterone analyte and/or reader devices of the disclosure. In one aspect, a kit is provided for determining qualitatively or quantitatively the presence of progesterone or a progesterone analyte and a second analyte in a biological sample, the kit comprising: a) an assay device configured to detect for at least the presence of progesterone or a progesterone analyte according to an embodiment of the disclosure; and b) instructions for using the kit.

In some cases, kits may include a one or more immunoassay test devices configured to detect for at least the presence of progesterone or a progesterone analyte of the disclosure. In some cases, the kit may provide a plurality of immunoassay devices configured to detect for at least the presence of progesterone or a progesterone analyte to enable a user to conduct a test on more than one occasion. In some cases, the immunoassay devices are configured for a single use (i.e., are disposable). A kit may include a plurality of test devices to enable a user to perform a test once a day, once every 2 days, once every 3 days, once every 4 days, once every 5 days, once every 6 days, once every week, once every 2 weeks, once every 3 weeks, once every 4 weeks, once every 5 weeks, once every 6 weeks once every 7 weeks, once every 8 weeks or more.

In some cases, kits may include a plurality of immunoassay devices, each capable of detecting at least the presence of progesterone or a progesterone analyte along with another analyte of the same type. In other cases, kits may include a plurality of immunoassay devices, each capable of detecting at least the presence of progesterone or a progesterone analyte and other different analytes. In a particular embodiment, a kit may include a plurality of immunoassay devices, each of the immunoassay devices capable of detecting the presence of progesterone or a progesterone analyte and LH in a biological sample. In another particular embodiment, a kit may include a plurality of immunoassay devices, each of the immunoassay devices capable of detecting the presence of progesterone or a progesterone analyte and hCG in a biological sample. In another particular embodiment, a kit may include a plurality of immunoassay devices, each of the immunoassay devices capable of detecting the presence of progesterone or a progesterone analyte and E2 in a biological sample. In another particular embodiment, a kit may include a plurality of immunoassay devices, each of the immunoassay devices capable of detecting the presence of progesterone or a progesterone analyte and FSH in a biological sample. In an embodiment, the immunoassay device may include progesterone or a progesterone analyte in addition to two or more of the additional hormones mentioned in this paragraph. Each of these configurations of immunoassay devices are described further in the present applicant's previous filings, including U.S. patent application Ser. No. 15/974,229, filed on May 8, 2018 claiming priority to U.S. Provisional Patent Application 62/503,223 Filed on May 8, 2017, a claim of priority made to each of which herein, and each of which are incorporated by reference in their entirety herein. These immunoassay devices are further described in U.S. patent application Ser. No. 16/381, 229 filed Apr. 11, 2019, which is a national stage application of PCT Application No. PCT/US18/68027, filed Dec. 28, 2018, which is a PCT application claiming priority to U.S. Provisional Application No. 62/611,467 filed Dec. 28, 2017.

More specifically, the present inventor has recognized that due to the many drawbacks associated with serum testing for progesterone levels at one point in time as is commonly practiced, what is instead necessary to more effectively evaluate corpus luteum functionality involves a series of single tests to track progesterone levels (optionally, by evaluating analytes of progesterone in urine that correlate to serum progesterone levels) daily over a period of multiple days. To efficiently facilitate such testing, the method utilizes a number of single tests each configured to evaluate non-serum bodily fluids for the presence of at least progesterone or metabolites of progesterone above a pre-defined threshold level.

The non-serum bodily fluid evaluated via the preferred embodiment of the present invention is urine. To effectively facilitate the method when the non-serum bodily fluid tested is urine, the present inventor has discovered that the best time to collect a sample is immediately after the woman whose corpus luteum is under evaluation wakes up from the longest sleep period of the preceding twenty four hours. The present inventor has noted that this sample consisting of the first morning urine presents a more accurate representation of the previous day's serum progesterone levels.

In an intended use of an embodiment of the system, the present inventor has devised a method for determining functionality of the corpus luteum utilizing specialized testing devices which in an aspect form a part of the system, optionally single tests, depicted in FIG. 1. In various embodiments, the specialized testing devices evaluate non-serum bodily fluids for at least the presence of progesterone or at least one analyte of progesterone. In various embodiments, the testing devices are configured to detect for the presence of Pregnandiol Gluclorinide (PdG) in urine. In the preferred embodiment, the single tests comprise one or more test strips 3001 as further described in U.S. patent application Ser. No. 16/544,554 filed on Aug. 19, 2019, already incorporated by reference herein. In alternative embodiments, the single tests comprise devices to detect for the presence of progesterone in saliva, which optionally may consist of the testing devices described in United States Patent Application Publication US20180106799A1, which is incorporated by reference herein in its entirety. The present inventor has recognized that the methods contemplated herein, in an example, may be utilized in conjunction with a base unit configured read a single test configured to detect for the presence of progesterone in saliva. Optionally, such saliva-based test is configured to detect the presence of progesterone in saliva above or below a threshold set at a value selected from the range of 90-300 pg-ml, which the present inventor recognizes corresponds to a level corresponding to proper Corpus Luteum functioning in a wide range of women.

The inventive method in its preferred form incorporates the step of predicting a date to optimally conduct testing 1001. In an example, the ovulation date is first estimated. During this step, the ovulation date is estimated by sampling cervical mucus, retrieving a basal body temperature, or utilizing lateral flow assays configured to detect for the presence of lutenizing hormone (LH) to predict ovulation. Optionally, the lateral flow assay may be configured as a test strip able to evaluate urine for the presence or absence of PdG on within multiple testing zones on the same strip. In an example, the estimated ovulation date is utilized to calculate the optimal date or range of dates to perform a test to evaluate a bodily fluid for the presence or absence of any of progesterone, PdG, LH, HcG or Estrogen. Optionally, the ovulation date is utilized to calculate the optimal date or range of dates to conduct bodily fluid testing.

Then, following the predicting an ovulation date step, the method preferably includes a collecting step 1002. During the collecting step 1002, a non-serum bodily fluid sample daily is collected for at least three consecutive days. In the case where the non-serum bodily fluid collected is urine, the sample may be collected within a cup during urination. In some instances, where the testing device is configured to allow the urine sample to be collected mid-stream during urination, the urine sample may be collected directly onto the testing device. In the preferred method where the non-serum bodily fluid collected is urine, the urine consists of a urine sample taken in the morning during the first urination after the subject awakens from overnight sleep or the longest sleep of the day (referred to as "first morning urine"). Alternatively, in the case where the non-serum bodily fluid sample collected is saliva, the sample may be collected with a swab. The collection step during the preferred method takes place between 7-10 days past the predicted ovulation date. In any case, the objective of the step is to collect enough of a sample to allow for the non-serum bodily fluid to be temporarily held as needed, and then evaluated by a testing device.

Then, following the collecting step 1002, a testing step 1003 takes place. During the testing step, for each non-serum bodily fluid sample, a testing device is used to evaluate the non-serum bodily fluid sample for the presence of progesterone or a metabolite of progesterone. In the preferred method, the testing step 1003 utilizes a single test consisting of a single-use disposable non-serum bodily fluid test configured to detect for at least progesterone or a metabolite of progesterone above a pre-defined threshold. In an embodiment of the invention, the non-serum bodily fluid test is configured to evaluate urine for the presence of at least one metabolite of progesterone, optionally PdG, above a threshold of 5 ug/mL. In an embodiment, the pre-defined threshold is determined from a value chosen from a sliding scale. In an embodiment, a threshold from within the scale's range is a value within the range of 3-10 ug/ml. During the testing step 1003, the single test indicates whether progesterone or a metabolite of progesterone is present in the tested non-serum bodily fluid sample above a pre-defined threshold. Optionally, the threshold amount may be set to the minimum amount of progesterone or progesterone analyte corresponding to the amount of minimum amount of progesterone needed to be present in the bloodstream to indicate that ovulation has occurred. A result indicated by the single test of "positive" means that the level of progesterone or analyte of progesterone present in the tested non-serum bodily fluid sample has exceeded the pre-defined threshold. A result indicated by the single test of "negative" means that the level of progesterone or analyte of progesterone present in the tested non-serum bodily fluid sample has not exceeded the pre-defined threshold. In an related example, a result indicated by the single test of "positive" could further indicate that the woman has entered into her infertile phase, and may thereby engage in sexual intercourse without the risk of unintended conception.

Then, following the first positive result indicated by the single test, indicating the presence of progesterone or a metabolite of progesterone above a pre-defined threshold in the tested non-serum bodily fluid sample, or the first fold change, a repeating step 1004 takes place. During the preferred method, the repeating step 1004, the collecting step 1002 and the testing step 1003 are performed over and over on a daily basis until the first negative result for progesterone or PdG displayed on the single test, indicating that progesterone or a metabolite of progesterone is below the pre-defined threshold. Alternatively the repeating step 1004 takes place daily for only 3 consecutive days, or for 4-10 days, regardless of the results displayed on the testing device. The present inventor has recognized that performing the repeating step 1004 multiple times during a fixed period of time, ideally a timeframe chosen from the range of 3-10 days, occasionally has the effect of mitigating errors displayed on the single test.

Following the conclusion of the repeating step 1004 or multiple repeating steps 1004, where one or more additional iterations of the collecting step 1002 and the testing step 1003 have taken place, a recording step 1005 takes place. During the recording step 1005, the total number of days that the single test has indicated a positive result for progesterone or PdG, each positive result indicating the presence of progesterone or a metabolite of progesterone above the pre-defined threshold at the time of testing, prior to the first negative result for progesterone or PdG displayed on the single test, is recorded. Such recordation may optionally take place with the assistance of a calendar or similar application operating on a mobile device. Such application may optionally also allow its user to record results for testing devices that evaluate bodily fluids for Lutenizing Hormone (LH), Follicle Stimulating Hormone (FSH), and/or Estrogen or Estrogen metabolites.

Figure 3:
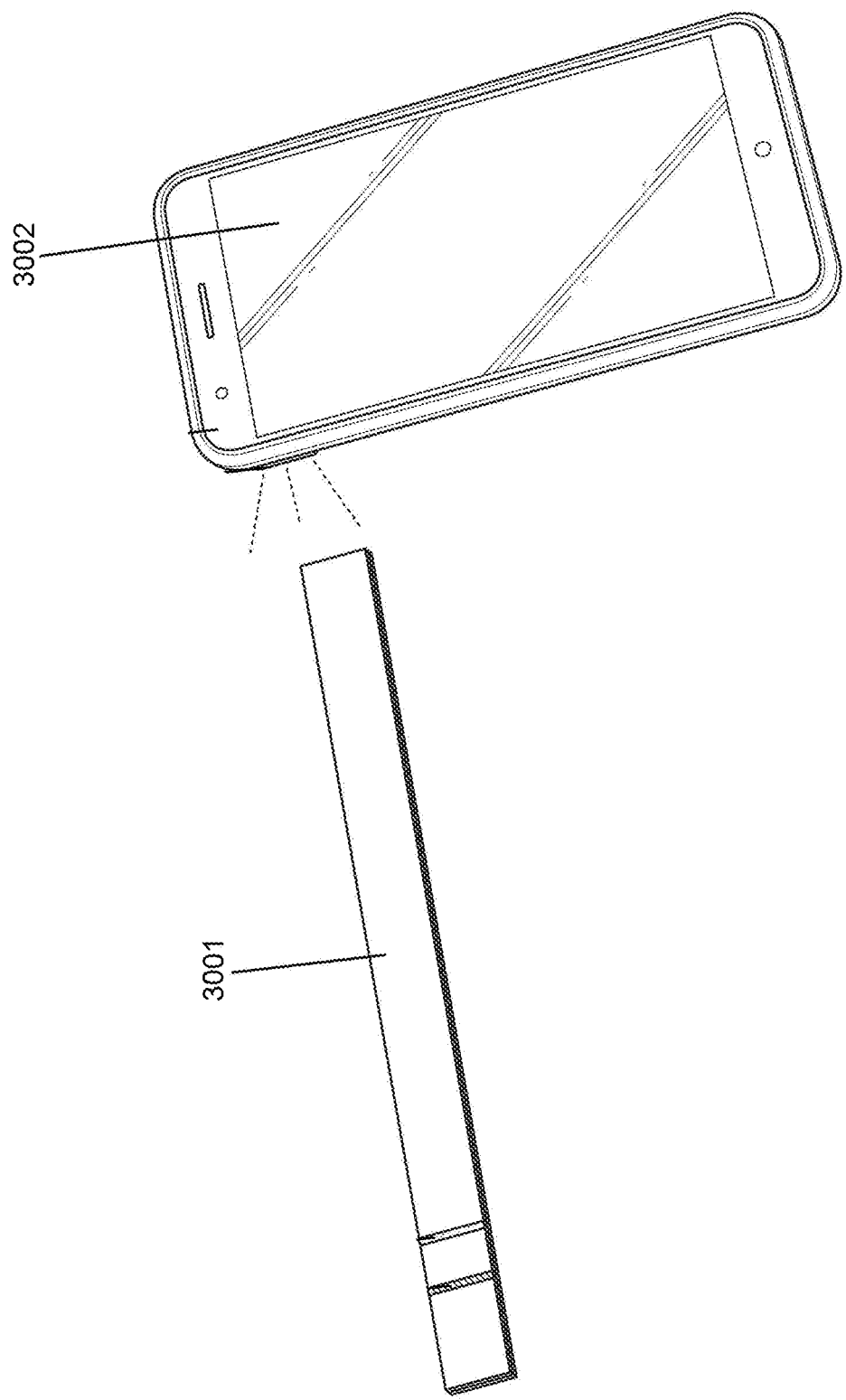
FIG. 3 depicts an embodiment featuring the use of an application operating on a mobile device featuring a camera.

The present inventor has noted that a mobile device operating an application featuring the ability to facilitate the recording step 1005 described above. In an example of the invention, an application operating on a mobile device featuring a camera, as depicted in FIG. 3, may be configured and utilized to photograph the results of a single test, and near-simultaneously interpret and record the results of each single test. The present inventor has noted that this example of the method is particularly helpful in instances where a single test incorporates one or more test strips 3001 configured to evaluate for multiple hormones and/or analytes, as is further described in U.S. patent application Ser. No. 16/381, 229, filed on Apr. 11, 2019, incorporated by reference herein in its entirety. In one embodiment, the test strip used in accordance with the method described herein is configured to evaluate urine for the presence of PdG and LH.

Figure 2:
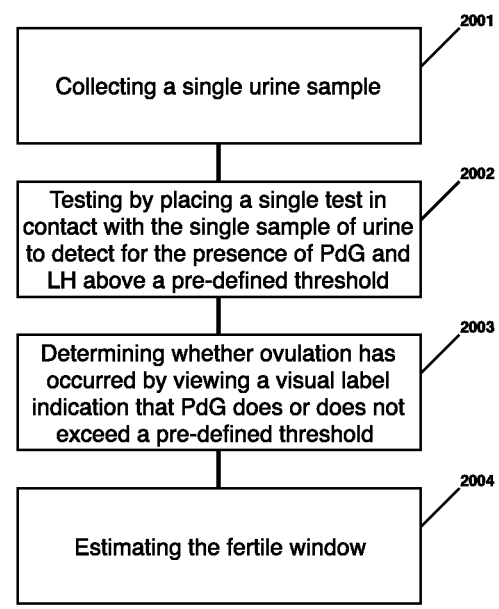
FIG. 2 shows method steps associated with a method to estimate the fertile window in association with corpus luteum functionality.

Corpus luteum functionality and fertility and the fertile window within the menstrual cycle are closely related. In a related method, depicted in FIG. 2, following the step of collecting a single sample of urine 2001 optionally consisting of a woman urinating into a cup, a testing step 2002 follows. During an exemplary testing step, a single test configured to evaluate urine is placed into contact with the previously collected single sample of urine and utilized to detect for whether both PdG and LH are present in the single sample of urine, each above a pre-defined threshold. Following the testing step, a step of determining whether ovulation has occurred 2003 follows. During an exemplary determining whether ovulation has occurred step, an indication on a single test that PdG exceeds a predefined threshold, optionally 5 ug/mL, signals that ovulation has occurred. In an example, the indication by the test strip 3001 that ovulation has occurred is presented by a visual label. In an example, the visual label is perceptible by the human eye. In an alternative example, the visual label consists of fluorescent dye imperceptible to the human eye readable only with the assistance of a machine, optionally a base unit 4001 or digital reader 3002. Following the determining whether ovulation has occurred step, a step of estimating the fertile window 2004 occurs. During an example of such step, the fertile window is estimated by calculating a number of days, optionally two days, following the first positive indication of LH after a negative indication for LH from the immediately preceding day's testing. The estimating the fertile window step also optionally comprises confirming a negative indication for PdG in urine, as a positive indication would signify that the fertile window has closed as the presence of PdG correlates to prior ovulation.

To further illustrate, in a series of tests associated with the methods described herein, if the following occurs, ovulation may be confirmed over a three tests on three separate days to aid in the estimation of the functionality of the corpus luteum and a prediction of the fertile window:

Example 1—test one results in readings of PdG below a pre-defined threshold and LH below a pre-defined threshold; test two results in PdG above a pre-defined threshold and LH above a pre-defined threshold; test three results in PdG above a pre-defined threshold and LH below a pre-defined threshold. This Example 1 signifies that following an LH surge indicating the follicle maturation, that progesterone released indicating ovulation. Such a result demonstrates proper corpus luteum functioning.

Example 2—test one, results in readings of PdG below a pre-defined threshold and LH below a pre-defined threshold; test two results in readings of PdG below a pre-defined threshold and LH a pre-defined threshold; test three results in readings of PdG a pre-defined threshold and LH above a pre-defined threshold. This Example 2 signifies that following a sustained LH surge indicating follicle maturation, that progesterone released indicating ovulation. Such a result demonstrates proper corpus luteum functioning.

Example 3—test one results in PdG below a pre-defined threshold and LH below a pre-defined threshold; test two results in PdG above a pre-defined threshold and LH below a pre-defined threshold. This Example 3 signifies that either the LH surge was missed by the test results or that urine was too diluted to detect the LH surge, but regardless that progesterone was released indicating ovulation. Such a result demonstrates proper corpus luteum functioning. Such result also highlights the importance of multiple day testing utilizing disposable test strips 3001 in accordance with the methods described herein as opposed to single point testing.

To further illustrate, in a series of tests, if the following occurs, a potential problem with the functionality of the corpus luteum may be detected:

Example 4—test one, results in readings of PdG below a pre-defined threshold and LH below a pre-defined threshold; test two results in readings of PdG below a pre-defined threshold and LH above a pre-defined threshold; test three results in readings of PdG below a pre-defined threshold and LH below a pre-defined threshold. Such a result indicates the possibility of improper corpus luteum functioning. As no progesterone (or its analyte, PdG) was detected during this exemplary series, it is possible that the relevant corpus luteum is not functioning properly to support implantation.

In embodiments of the invention, the tests utilized (optionally a "single test" which as used herein comprises one or more test strips 3001 that are disposable and altogether intended to be utilized one time to evaluate a single non-serum bodily fluid sample) incorporate a pre-defined threshold of PdG correlating in a positive result to at least the lowest amount of progesterone present and necessary to support conception. In embodiments of the invention, the tests utilized (optionally a single test) incorporate a pre-defined threshold of LH correlating in a positive result to at least the lowest amount of LH necessary to fully mature a follicle and cause rupture). In an embodiment of the invention, the pre-defined threshold of PdG is determined by a fixed amount of PdG antibody on the conjugate pad and the amount of PdG conjugate impregnated on the membrane in competitive assay form. In an embodiment of the invention, the pre-defined threshold of LH is determined by a fixed amount of LH antibody on the conjugate pad and the amount of LH antibody on the membrane in sandwich assay form. In an embodiment of the invention, the sandwich assay form and the competitive assay form are integrated together into a single test. In an embodiment of the invention, the receiving zones containing the LH antibody and the PdG antibody, and optionally antibodies of other hormones or analytes including FSH, Estrogen analyte, and hCG, are incorporated into a single conjugate pad within a single test. In an alternative embodiment of the invention, the receiving zones containing the LH antibody and the PdG antibody, and optionally antibodies of other hormones or analytes including FSH, Estrogen analyte, and hCG, are incorporated into at least two discrete conjugate pads within a single test. In an embodiment of the invention, the test strip 3001 is configured to incorporate multiple visual labels, including a test line 3003 and a visual label indicating the absence or presence of PdG 3006, a visual label indicating the absence or presence of LH, 3007, and a visual label indicating the absence or presence of estrogen or an analyte of estrogen 3008, as depicted in FIG. 4B. In an embodiment of the invention, the pre-defined threshold of PdG and/or the pre-defined threshold of LH is determined by a percentage difference from a previous test, optionally indicating a trend or fold change. In an embodiment, the test is contained within a cartridge. Optionally, the test or cartridge surrounding the test further incorporates an identifying feature, such as a QR Code, bar code or lot number, to identify the specific test and/or corresponding results. An example of such a single test incorporating such an identifying feature is further described in United States Patent Application Publication US 2018/0196037 A1 published on Jul. 12, 2018, which is hereby incorporated by reference in its entirety. In an embodiment, each conjugate pad may comprise antibodies conjugated to the same visual dye or different visual dyes.

In association with the above described method and other methods of use, a suitably configured single test able to detect for the presence of at least PdG or Progesterone in a bodily fluid is useful, which in an embodiment forms a part of the system. Such a single test optionally comprises one or more test strips 3001 described with particularity in U.S. Patent Applications No. 62/720,953, filed on Aug. 22, 2018; Ser. No. 15/974,229 filed May 8, 2018; and Ser. No. 16/381,229 filed Apr. 11, 2019; the entire contents of said applications hereby incorporated by reference. Referring now to FIG. 4, a test strip 3001 of the present invention is shown wherein an end with a sample pad is dipped into a urine sample such that the urine sample flows up the test strip 3001 in a direction depicted by an arrow and is stopped by an adsorbent pad at an end opposite the sample pad. The sample pad is readily available from various supplies, such as SureWick Pad Materials from Millipore Sigma. The test strip 3001 includes a conjugate pad that can be a glass fiber conjugate pad saturated with colloidal gold, colored latex beads or other visual dye particles that are conjugated to anti-pregnanediol gluconoride mouse monoclonal antibodies. A membrane of the test strip 3001 can be a nitrocellulose membrane with pore size between 3 to 20 µm. At least a test line configured to detect for the presence or absence of PdG in the tested fluid 3006 and a control line 3003 are impregnated on the membrane. The membrane is supported by a backing card.

The present inventor has discovered a unique combination of specific elements to allow for the detection of pregnanediol glucuronide (PdG) formulated such as to enable the creation of a pregnanediol glucuronide (PdG) urine test. In the preferred embodiment of the invention, Bovine Gamma Globulin (BGG) is conjugated with PdG and combined with a mouse anti-PdG antibody of IgG2b isotype binding partner. In an alternative embodiment of the invention Bovine Gamma Globulin (BGG) conjugated to PdG is combined with a mouse anti-PdG antibody of IgG1, IgG1 Kappa, IgG2a or IgG2c isotype. The present inventor has recognized that such a specific combination uniquely allows for colloidal gold to be conjugated to the anti-PdG antibody of one of the specific isotypes mentioned above, and for the colloidal gold conjugated anti-PdG antibody to interact with the PdG-BGG conjugate. Other combinations have been attempted, and have failed to allow the colloidal gold to function to produce the color needed to allow the test results to be viewable visually by the naked and untrained (layperson) eye. The present inventor has noted that the utilization of BGG conjugated to PdG allows for anti-PdG antibody, specifically of the IgG2b isotype, to bind in such a manner that colloidal gold is carried at a concentration sufficient for naked eye visualization. The present inventor notes that Globulins evidence the preferable binding ratio of 8-32 PdG antigens per carrier protein, which favor presentation of a visual result perceptible to the naked eye or to a reader. It is therefore a teaching of embodiments of the invention to comprise a carrier protein demonstrating the binding ratio of 8-32 PdG antigens per carrier protein. The present inventor has recognized the benefit associated with embodiments of the invention described herein that a PdG test may be producible allowing the results to be visually interpreted with the naked eye. The present inventor has recognized the benefit associated with embodiments of the invention that a PdG test may be producible allowing the results to be visually interpreted with the naked eye.

The present inventors have recognized the benefit of a configuration of an embodiment of the invention, embodied as a test strip configured to simultaneously analyze a non-serum bodily fluid beyond mere analysis for the presence of pregnanediol, by further analyzing up to six (6) analytes and/or hormones in an alternative test strip 1001 configuration featuring a testing zone configured to evaluate the non-serum bodily fluid for the presence of PdG beyond a specific threshold and optionally additional testing zones. In an embodiment, the test strip comprises a testing zone configured to evaluate urine for the presence of PdG beyond a specific threshold, and at least a second testing zone. It is a teaching of an embodiment of the present invention for the test strip to optionally incorporate one or more additional testing zones beyond the testing zone configured to analyze urine for the presence of PdG, each additional testing zone specifically configured to evaluate urine for the presence of an item selected from the group consisting of LH, HCG, FSH, Testosterone and/or Estrogen or analytes thereof, such as E3G.

In an embodiment, the test strip is configured to simultaneously indicate, in a testing zone, a positive or negative result for the presence of PdG above a pre-set threshold in a sample of urine applied to the test strip, in addition to indicating, in at least a second testing zone, a positive or negative result for the presence of at least one additional analyte and/or hormone, and, optionally, indicating in an additional third testing zone, a positive or negative result for the presence of at least one additional analyte and/or hormone, all contained within a single test strip. In an embodiment of the invention, the at least one additional analyte and/or hormone to be tested within at least the second testing zone is selected from the following group: (1), Estradiol (E2) at a concentration selected from the range inclusive of 25-3,000 pg/ml in a competitive assay format or any urine metabolites of Estradiol, such as for instance Estrone-3-Glucuronide (E3G), in the following ranges of concentrations: 1-1000 ng/ml in a competitive assay format; (2), Follicle Stimulating Hormone (FSH) at a concentration selected from the range inclusive of 1-30 mIU/ml in a sandwich assay format; (3), Luteinizing Hormone (LH) at a concentration selected from the range inclusive of 1-50 mIU/ml in a sandwich assay format; (4), Progesterone (P4) at a concentration selected from the range inclusive of 1-60 ng/ml in a competitive or sandwich assay format; (5) human chorionic gonadotropin, (hCG) at concentration selected from the range inclusive of 1-10,000 mIU/ml; (6) Testosterone, at concentrations of 1 to 50 µg, in a competitive assay format. In an embodiment, the analyte and/or hormone that the test strip 1001 will simultaneously measure in at least a second testing zone and optionally a third testing zone are selected from the group consisting of E2, FSH, LH, P4, Testosterone, E3G and HcG. In an embodiment, the second testing zone is configured to detect for the presence of a hormone or analyte differing from the hormone or analyte detected by the third testing zone. In an embodiment, a digital reader is configured to evaluate the second testing zone and optionally the third testing zone in association with the methods further described herein. In an embodiment, the test strip further incorporates, in addition to a testing zone, a second testing zone, and a third testing zone, a fourth testing zone configured to similarly detect for the presence of a hormone or analyte differing from the hormone or analyte detected by the other (first, second and third) testing zones within the test strip. The methods of evaluation and further configurations optionally applied to the test strip 1001 associated with the testing of analytes and/or hormones beyond and in addition to pregnanediol are further described in U.S. patent application Ser. No. 15/974,229, filed on May 25, 2018, which is hereby incorporated by reference in its entirety.

In an embodiment of the invention, labels (such as colloidal gold) are varied, with a separate and distinct label configured to attach to a separate hormone. In such embodiment, the present inventor has recognized the advantage that the test strip is configured to provide a different color for each hormone analyte indicating either the presence or absence of each hormone analyte following application of urine to the test strip. In an embodiment, the test strip is configured to comprise a conjugate pad (the conjugate pad also referred to as the "receiving zone" herein) comprising anti-PdG antibody-collodial gold conjugate, and at least one other conjugate. In an embodiment, the at least one other conjugate comprises anti-LH antibody-conjugated with a different label, optionally differently colored latex beads.

The present inventor has recognized that LH and HCG commonly exhibit cross-reactivity, specifically due to the fact that HCG can bind to LH antibodies. Therefore, having different colors corresponding to the presence of different hormones provides a benefit by allowing an observer to determine whether cross-reactivity has taken place. In other words, if an area designated to test for the presence of LH displayed the coloration of the label for HCG, one skilled in the art would understand such a read to indicate that cross-reactivity has been demonstrated and that the test therefore is invalid. Alternatively, the present inventor has noted that due to the similarities in structure between estrogen analytes and progesterone analytes (in at least one example, said progesterone analytes consisting of PdG), cross reactivity could take place between those two hormone metabolites specifically. Thus, it is beneficial to have different hormones or hormone metabolites labelled with different colors. Such labelling is accomplished in an embodiment by binding to colloidal gold and/or one or more differently colored latex beads, each testing zone within the strip featuring a differently colored label, and is therefore a teaching of an embodiment of the invention.

The present inventor has discovered that because PdG is a small hormone metabolite, in order to strongly bind to the surface of a membrane, PdG requires a strong carrier protein, which is a teaching of an embodiment of the invention. However, the present inventor has discovered that, for the preferred embodiment of the invention to function as intended, not only does the strong carrier protein need to bind the nitrocellulose membrane of the test strip, but the strong carrier protein also needs to bind the PdG and present it to the anti-PdG antibody, which is a teaching of an embodiment of the invention.

Such teachings as disclosed herein, solve the challenges associated with suboptimal prior art teachings, which lacked the ideal combination of a strong carrier protein able to bind the PdG and present it to the anti-PdG antibody.

In accord with teachings of the invention, the test strip relies on the certain reagents being able to interact with other reagents to produce color in the testing zone of the membrane. Specifically, in the absence of PdG hormone in the urine sample, the following reagents must interact in order for the test results to be useful. First, in the preferred embodiment, colloidal gold must be conjugated to the immunologically active anti-PdG antibody of one of the specific IgG isotypes described elsewhere herein. In alternative embodiments, as a replacement for colloidial gold in other embodiments described herein, an alternative visual dye such as latex beads may be utilized to a similar effect. Further, in embodiments of the invention, the colloidal gold conjugated anti-PdG antibody must interact with the PdG-carrier protein conjugate. Moreover, the PdG-carrier protein must bind a nitrocellulose membrane. The present inventor has recognized that for these embodiments to function as intended, these interactions between and among the colloidal gold conjugated anti-PdG antibody and the PdG-carrier protein conjugate, must be strong enough and stable enough to form and stay bound during urine sample application and lateral flow of the fluid across the reaction zone to solve the problems faced by the suboptimal prior art mechanisms described elsewhere herein. The disclosures in this paragraph constitute teachings of an embodiment of the invention.

In association with teachings of the invention, the test strip is configured to comprise a conjugate of a carrier protein demonstrating the binding ratio of 8-32 PdG antigens per carrier protein, optionally a Globulin carrier protein, with PdG. Such PdG-carrier protein conjugate is combined with a mouse anti-PdG antibody of one the class of the IgG isotypes in an embodiment. The class of Ig isotypes includes IgG1, IgG2b, IgG1 Kappa, IgG2a or IgG2c isotype as contemplated in association with embodiments of the invention. The conjugation of a carrier protein to PdG, and the combination of the PdG-conjugated carrier protein with a mouse anti-PdG antibody of Ig isotype is accomplished in accord with general conjugation procedures as well-known by those skilled in the art. In embodiments of the invention, one carrier protein is conjugated to eight or more PdG molecules. In the preferred embodiment, the one carrier protein is conjugated to no more than thirty two PdG molecules. The present inventor has discovered that such a ratio allows for the colloidal gold conjugated anti-PdG antibody to bind with both enough affinity and avidity to produce a bright enough color in the test reaction zone for typical users to distinguish visually. The present inventor has discovered the specific property of Globulin enabling such combination. In embodiments of the invention, as Globulin exhibits the optimal number of active sites optimally spaced, the inclusion of Globulin results in a lesser amount of steric hindrance, and therefore embodiments of the invention are enabled to receive and bind PdG at sufficient ratios. Therefore, Globulin is essential for the preferred embodiment of the invention to function as intended. In the preferred embodiment of the invention, therefore, PdG is conjugated to a Globulin. In embodiments of the invention, the testing zone is configured to comprise a progesterone metabolite, optionally pregnanediol (PdG), conjugated to a Globulin carrier protein at a concentration of a value selected from the range of 0.5 pg/ml-2 pg/ml within the testing zone. In an embodiment of the invention, the Globulin carrier protein consists of Bovine Gamma Globulin (BGG). The present inventor has recognized that the application of the PdG-carrier protein conjugate at the concentration levels described above, when applied to the test strip in conjunction with the application of the anti-PdG of a specified IgG isotype conjugated to a visual label of the specific concentration levels described herein, accomplishes the proper ratio of those specific binding partners to enable the test strip to detect for the presence of PdG in a sample of urine applied to the test strip at the pre-defined thresholds described above and further visually indicate that the sample of urine contains PdG above the pre-defined threshold or visually indicate that the sample of urine does not contain PdG above the pre-defined threshold. During a configuration step associated with conjugating in an embodiment, PdG is conjugated to a specified Globulin as a carrier protein, and, separately, a mouse anti-PdG antibody chosen from the group of isotypes including IgG1, IgG1 Kappa, IgG2a, or IgG2c is conjugated to colloidal gold. In the configuring step, to create the Test strip, the PdG-Globulin conjugate is impregnated or striped onto the nitrocellulose membrane in the testing zone of the test strip. Colloidal gold conjugated anti-PdG antibody is applied or soaked into the receiving zone of the test strip. When a fluid sample containing PdG is applied, the free PDG will bind to the anti-PDG antibody and travel to the testing zone of the test strip. Any unbound anti-PDG antibody will bind to the testing zone area and produce a colored line. In this type of competitive assay format, the absence of color in the testing zone indicates a positive test result for the presence of a progesterone metabolite, and the presence of color in the testing zone indicates a negative result for the presence of a progesterone metabolite. The present inventor notes that advantages exist within the broader category of Globulins as carrier proteins of PdG, thus various embodiments of the invention utilize one of the Globulins as a carrier protein. utilization of a Globulin conjugated to PdG allows for anti-PdG antibody of an immunologically active IgG isotype, to bind in such a manner that colloidal gold is carried at a concentration sufficient for naked eye visualization, and is therefore a teaching of embodiments of the invention. The present inventor notes that Globulins generally evidence the preferable binding ratio of 8-32 PdG antigens per Globulin, which favor presentation of a visual result perceptible to the naked eye or to a reader, and is therefore a teaching of embodiments of the invention. The inventor notes, however, that other non-Globulin carrier proteins may bind to PdG in accordance with the preferable binding ratio of 8-32 PdG antigens per carrier protein. For example, as described in U.S. Pat. No. 7,144,742 dated Dec. 5, 2006 and incorporated by reference, a method of Conjugation of Pregnanediol Glucuronide to Bovine Serum Albumin (PDG-BSA Conjugate) is described. Bovine serum albumin, 40 mg, (Armour) was dissolved in 3.96 ml 0.10 M sodium bicarbonate sodium carbonate buffer, pH 9.0, and chilled in ice water. The dimethylformamide solution of PDG sulfo-N-hydroxysuccinimide ester, 848 mg, was added slowly with rapid stirring over 10 minutes to give an opalescent solution. The solution was incubated at 18-25° C. for 6.5 hours. It was them applied to a 40 cm3 column containing Sephadex G-25 (Pharmacia) equilibrated with PBS buffer to separate the conjugated protein from unconjugated PDG, dimethylformamide, and reaction products. The conjugate was stored frozen at −20° C. The present inventor has recognized the benefit associated with the embodiments of the invention as described herein in that a PdG test may be producible allowing the results to be visually interpreted with the naked eye. In embodiments of the invention, the carrier protein comprises one of the following human, non-human, or plant globulins: vicilin, legumin, casein, Alpha 1-antichymotypsin, seruam amylid A, Alpha 1-lipoprotein, Haptogolulin, Alphy 2-antiplasmin, Protein C, Angiotensinogen, cortisol binding protein, beta-2 microglobulin, plasminogen, angiostatins, sexhormone-binding protein, transferrin, fibronectin, microglobulin, gamma globulin, thyroglobulin, 11S globulin family, 7S family of globulins. In various embodiments, the Globulin serving as the carrier protein derives from a plant or animal source, including an animal source such as human, mouse, rat, bovine, equine, goat, or rabbit. The present inventor notes that while Globulin carriers more generally demonstrate the favorable conjugation ratio of 8-32 antigens per one carrier protein, other non-Globulin carrier proteins such as Bovine Serum Albumin may be present in a PdG-carrier protein conjugate and still accomplish the favorable ratio of 8-32 antigens per one carrier protein in accordance with mechanisms to increase conjugation ratios as well known in the art.

It is a further teaching of the invention that in order for the preferred embodiment of the invention to function as intended, the specifically chosen anti-PdG antibody needs to be monoclonal, due to the nature of the PdG antigen presentation on the PdG-carrier protein conjugate. In order for the embodiments of the invention to function as intended, the specifically chosen anti-PdG antibody must incorporate one of the following isotypes: IgG1 (including IgG1 Kappa), IgG2a, IgG2b, or IgG2c. The present inventor has discovered that isotypes other than IgG1 (including IgG1 Kappa), IgG2a, IgG2b, or IgG2c, including but not limited to IgM, IgS, and IgE anti-PdG antibody isotypes, remain unable to effectively bind the colloidal gold (or other visual label) and produce a strong enough color signal on the reaction zone due to their size and structure and are therefore excluded from the preferred embodiment of the invention. Since the colloidal gold must bind the Ig region of the anti-PdG antibody, the present inventor has discovered that the IgG1 (including IgG1 Kappa), IgG2a, IgG2b, and IgG2c isotypes of the anti-PdG antibody sufficiently bind colloidal gold and are therefore incorporated into embodiments of the invention. As a result, the IgG1 (including IgG1 Kappa), IgG2a, IgG2b and IgG2c isotypes of the anti-PdG antibody therefore produce the strongest color. In the preferred embodiment of the invention, the IgG2b isotype is included in the invention, as the present inventor has recognized that the IgG2b isotype performs slightly better when producing color. Therefore, the preferred embodiment of the invention incorporates the IgG2b isotype of the anti-PdG antibody. Alternative embodiments of the invention incorporate the IgG2a, IgG2c or IgG1 (including IgG1 Kappa) isotypes of the anti-PdG antibody.

As referred to herein, a monoclonal anti-PdG antibody as described in the preceding paragraphs, and more specifically a monoclonal anti-PdG antibody having the necessary binding affinity for PdG such that when used in association with the invention as described herein it is capable of yielding a detection threshold of PdG of 3-20 µg/mL, has been deposited in accordance with the provisions of the Budapest Treaty at the American Type Culture Collection (ATCC), located at the following address: 10801 University Boulevard, Manassas, Va. 20110 USA on Apr. 23, 2021. The accession number of the deposit is Patent Deposit Number PTA-127054. The deposited material is a biological material specifically identified in the application, namely a monoclonal anti-PdG antibody as specifically referred to herein, and more specifically an anti-PdG antibody as described in the preceding two paragraphs and elsewhere herein.

The present inventor has recognized that the utilization of a Globulin within a specific combination uniquely allows for colloidal gold to be conjugated to the immunologically active anti-PdG antibody of one of the class of the IgG isotypes. In an embodiment, the combination enables the colloidal gold conjugated anti-PdG antibody to interact with the PdG-Globulin conjugate. In embodiments of the invention, therefore, the conjugate striped on the membrane in the testing area is PdG-Globulin and the anti-PdG antibody must be a monoclonal anti-PdG antibody of one of the following isotypes: IgG1, IgG2a, IgG2b, or IgG2c.

The present inventor recognizes that embodiments of the invention differ from other combinations that have been attempted in the prior art. Specifically, the other combinations have failed to allow the colloidal gold to function to produce the color needed to allow the test results to be viewable visually by the naked and untrained (layperson) eye. The present inventor has recognized that the novel utilization of a Globulin conjugated to PdG as described herein allows for anti-PdG antibody specifically of the Ig isotype, in accordance with the specific concentration levels described herein in embodiments of the invention, to bind in such a manner that colloidal gold is carried at a concentration sufficient for naked eye visualization. The present inventor has recognized the benefit associated with embodiments of the invention that a PdG test may be producible allowing the results to be visually interpreted with the naked eye and/or an external reader affordable to a typical consumer.

In embodiments of the invention, one carrier protein is conjugated to eight or more PdG molecules. In the preferred embodiment, the one carrier protein is conjugated to no more than thirty two PdG molecules. The present inventor has discovered that such a ratio allows for the colloidal gold conjugated anti-PdG antibody to bind with both enough affinity and avidity to produce a bright enough color in the test reaction zone for typical users to distinguish visually.

In various embodiments of the invention, the test strip 1001 comprises at least one specially configured receiving zone. In an embodiment, the receiving zone serves to receive a bodily fluid sample which may contain the metabolite of interest and to begin the flow of the sample along the test strip 1001. The receiving zone is prepared from a natural or synthetic porous or macroporous material which is capable of conducting lateral flow of the fluid sample. A porous or macroporous material suitable for purposes of this invention generally has a pore size greater than 12 µm. Examples of porous materials include, but are not limited to, glass, cotton, cellulose, nitrocellulose, polyester, rayon, nylon, polyethersulfone, and polyethylene. In an embodiment, the test strip 1001 is configured to comprise an anti-PdG antibody of the IgG isotype conjugated to a visual label at a concentration of a value selected from within the range of 1 µg/ml-10 µg/ml within at least one receiving zone. In an embodiment, the test strip 1001 is configured to comprise an anti-PdG antibody conjugated to a visual label at a concentration of 7 µg/ml within at least one receiving zone. In various embodiments, the visual label consists of colloidal gold. In various embodiments, the colloidal gold particles chosen to make up the anti-PdG antibody-collodial gold conjugate are of a size dimension of a value selected from the range of 20-100 nm. In various embodiments, the colloidal gold particles chosen to make up the anti-PdG antibody-collodial gold conjugate are of a concentration of 0.7-1.3 OD. The present inventor has recognized that the application of the anti-PdG conjugated to a visual label at the concentration levels described above, when applied to the receiving zone of the test strip 1001 in conjunction with the application of the PdG-carrier protein conjugate of the specific concentration levels described herein applied to the testing zone of the test strip, accomplishes the proper ratio of those specific binding partners to enable the test strip to detect for the presence of PdG in a sample of urine applied to the test strip, and further visually indicate that the sample of urine contains PdG above the pre-defined threshold or visually indicate that the sample of urine does not contain PdG above the pre-defined threshold.

Therefore, in various embodiments of the invention, the present inventor has recognized that the test strip configured as described effectively and reproducibly produces a negative test result if the PdG level in tested urine is below approximately 5 µg/ml; and the Test strip configured as described effectively and reproducibly produces a positive test result if the PdG level in tested urine is above approximately 5 ug/ml. The present inventor recognizes that due to variations in the ability of different populations to metabolize progesterone in urine, the 5 µg/ml threshold is not always the appropriate threshold. Therefore, various embodiments of the Test strip 1001 are configured to display a positive or negative result based on pre-defined thresholds of a PdG level of a value selected from values within the range of 3 µg/ml-20 µg/ml. The present inventor has recognized that embodiments of the invention are appropriately used in association with tracking progesterone levels during pregnancy, since as pregnancy progresses, pregnanediol levels also increase. Therefore, having a predetermined threshold of a higher value (e.g. 10 µg/ml-20 µg/ml) allows the user to monitor pregnanediol levels through the duration of pregnancy. Such monitoring, with strips configured to measure pregnanediol with a pre-defined threshold from within the range of 10 µg/ml-20 µg/ml, allows the user to confirm that progesterone levels are increasing appropriately throughout pregnancy, and such configuration is incorporated as a teaching of an embodiment of the invention.

The preferred embodiment of the invention relies on the certain reagents being able to interact with other reagents to produce color in the test zone of the membrane. Specifically, in the absence of PdG analyte in the urine sample, the following reagents must interact in order for the test results to be useful. First, in the preferred embodiment, colloidal gold must be conjugated to the anti-PdG antibody (in the preferred embodiment, anti-PdG antibody having the IgG2b isotype). In alternative embodiments, as a replacement for colloidial gold in other embodiments described herein, an alternative visual dye such as latex beads may be utilized to a similar effect. Further, in embodiments of the invention, the colloidal gold conjugated anti-PdG antibody must interact with the PdG-BGG conjugate. Moreover, the PdG-BGG must bind the nitrocellulose membrane. The present inventor has recognized that for these embodiments to function as intended, these interactions between and among the colloidal gold conjugated anti-PdG antibody and the PdG-BGG conjugate must be strong enough and stable enough to form and stay bound during urine sample application and lateral flow of urine across the reaction zone to solve the problems faced by the suboptimal prior art mechanisms. In an embodiment configured to evaluate urine for hormones and/or analytes other than PdG in addition to PdG, a visual label having a distinct color is utilized to identify for the presence of each hormone and/or analyte tested. In one particular embodiment, a colloidal gold conjugated anti-PdG antibody is utilized to display or omits the color red to indicate the absence or presence of PdG within a sample and a latex bead conjugated anti-LH antibody is utilized to display or omit the color blue to indicate the absence or presence of LH within the same urine sample on the same test strip. In an embodiment, a test strip configured to evaluate urine for the presence of PdG and LH is contained within a cassette. In an embodiment, also further described in U.S. patent application Ser. No. 15/974,229, filed on May 8, 2018, incorporated by reference in its entirety herein, a disposable lateral flow assay tests cassette is configured to allow the sample to permeate through the one or more test strips 3001 into or through one or more detection zones, each optionally comprising a reagent-impregnated membrane, contained within each test strip. In an embodiment of the invention, the test strip in its novel configuration as described elsewhere herein is contained within a cartridge (also referred to as a "detection device"), and configured to be read within an associated base unit (also referred to as a "detection instrument") as further described within U.S. patent application Ser. No. 16/302,085, filed on Jul. 11, 2019, which is hereby incorporated by reference herein in its entirety. In an embodiment of the invention, the base unit consists of an improved version of the diagnostic test system as described in International Patent Application PCT/CN2017/095452 filed on Aug. 1, 2017 and in International Publication Number WO 2019/023926 A1, which are hereby incorporated by reference in its entirety, and the improvements of such diagnostic test system as described elsewhere herein, in one aspect such improvements including the novel methods of utilization.

For example, in some cases, the detecting of the presence or absence of hormones and/or analytes comprises: (A) illuminating the first capture region (as used herein, the term "capture region" is also referred to as "testing zone") and the second capture region with one or more light sources; (B) detecting the first optical signal from the first capture region and the second optical signal from the second capture region with one or more optical detectors; (C) determining an amount of the first analyte or hormone present in the biological sample based on a level of the first optical signal; and (D) determining an amount of the second analyte present in the biological sample based on a level of the second optical signal. In some cases, the first capture region is downstream of the second capture region on the test strip. In some cases, the second capture region is downstream of the first capture region on the test strip. In some cases, the first fluorescent label and the second fluorescent label are the same. In another aspect, an assay device is provided for determining a presence of at least a first analyte and a second analyte in a biological sample, the assay device comprising: a test strip defining a flow path and comprising: a) at a first end, a sample zone configured to be contacted with a biological sample suspected of containing the first analyte and the second analyte; b) a labeling zone having absorbed thereon a mobilizable first detection reagent conjugated to a first fluorescent label and a mobilizable second detection reagent conjugated to a second fluorescent label, which the first detection reagent specifically binds to the first analyte thereby forming a first analyte-first detection reagent complex and the second detection reagent specifically binds to the second analyte thereby forming a second analyte-second detection reagent complex; c) a capture zone comprising a first capture region and a second capture region, wherein the first capture region has immobilized thereon a first capture reagent which specifically binds to the first detection reagent when the first detection reagent is not in a complex with the first analyte, and the second capture region has immobilized thereon a second capture reagent which specifically binds to the second analyte-second detection reagent complex, wherein a first optical signal from the first fluorescent label is capable of being detected at the first capture region and which the first optical signal decreases with increasing amounts of the first analyte present in the biological sample, and wherein a second optical signal from the second fluorescent label is capable of being detected at the second capture region and which the second optical signal increases with increasing amounts of the second analyte present in the biological sample. In some cases, the first capture region is downstream of the second capture region on the test strip. In some cases, the second capture region is downstream of the first capture region on the test strip. In some cases, the assay device further comprises, downstream of the capture zone, a control zone comprising a first control region having immobilized thereon a first control reagent which binds to the first detection reagent and the second detection reagent, and a second control region having immobilized thereon a second control reagent which binds to the first detection reagent and the second detection reagent. In some cases, the assay device is configured to be inserted into a reader device for detecting the first and second optical signals from the first and second fluorescent labels. In some cases, the assay device further comprises a readable, or readable and writable chip, configured to be read and wrote by the reader device. In some cases, the readable chip comprises information related to the biological sample, the assay device, or both. In some cases, the first capture reagent does not displace the first analyte from the first detection reagent if the first analyte is bound to the first detection reagent. In some cases, the first capture reagent does not bind to the first analyte-first detection reagent complex. In some cases, the second capture reagent does not bind to non-complexed second analyte or non-complexed second detection reagent. In some cases, the first fluorescent label and the second fluorescent label are the same. In some cases, the first fluorescent label and the second fluorescent label are different. In some cases, the first detection reagent, the second detection reagent, or both is an antibody or antibody fragment. In some cases, the first detection reagent, the second detection reagent, or both is an antigen. In some cases, the biological sample is blood, urine, or saliva. In some cases, the first analyte is PdG and the second analyte is luteinizing hormone (LH) or estrone-3-glucuronide (E3G). In some cases, the first detection reagent is an anti-PdG antibody and the second detection reagent is an anti-LH antibody or an anti-E3G antibody. In some cases, the first capture reagent is a protein-E3G antigen complex and the second capture reagent is an anti-LH antibody. In some cases, a decrease in the first optical signal and an increase in the second optical signal are indicative of a time of an elevated ovulation cycle of a mammal. In some cases, the first control reagent and the second control reagent are anti-mouse IgG antibody. In another aspect, a diagnostic test system is provided, comprising: a housing, comprising: a) a port for receiving an assay device, the assay device comprising two or more capture regions; b) a reader comprising: i) one or more light sources for illuminating the two or more capture regions; ii) one or more light detectors for detecting optical signals from the two or more capture regions; and c) a data analyzer having one or more processors configured to: A) receive the optical signals; and B) determine an amount of at least a first analyte and a second analyte present in a biological sample based on the optical signals, wherein an optical signal of a first of the two or more capture regions increases with decreasing amounts of the first analyte present in the biological sample, and an optical signal of a second of the two or more capture regions increases with increasing amounts of the second analyte present in the biological sample. In some cases, the diagnostic test system is further configured to detect optical signals from two or more control regions on the assay device. In some cases, the diagnostic test system is further configured to compare optical signals from the two or more control regions with optical signals from the two or more capture regions. In some cases, the assay device comprises any assay device described above. In some cases, the assay device further comprises a second end, configured to be inserted into the port of the diagnostic test system. In some cases, the data analyzer is configured to detect an optical pattern of the optical signals. In some cases, the optical pattern is a binary optical pattern. In some cases, the assay device further comprises a readable chip configured to be detected by the reader. In some cases, the readable chip comprises information related to the biological sample, the assay device, or both. In some cases, the reader is configured to transmit a data output to a mobile device. In some cases, the data output comprises a medical result based on the amount of first analyte and the amount of second analyte present in the biological sample. In some cases, the optical signals are fluorescent signals. The device may be used to test for the presence or absence of at least a first analyte and a second analyte in a sample. In some cases, the device may be used to determine an amount or a relative amount of at least a first and second analyte in a sample. Other features of the immunoassay device may include a test strip cassette for supporting and/or protecting the test strip. The cassette may be composed of a sturdy material such as plastic (e.g., high-impact polystyrene). The cassette may include, at a proximal end, a sample application window for applying a fluid sample to the sample pad. The cassette may further include an assay results window for visualization of the assay results. The assay results window may be positioned on the device directly above the capture zone and control zone such that a detectable signal can be visualized or read (e.g., by a diagnostic test system). The cassette may be of a certain size and shape so as to be compatible with a diagnostic test device of the disclosure, such that the cassette may be inserted into a cavity, port or receiver of a diagnostic test device. In one aspect, a diagnostic test system is provided comprising: a housing, comprising: a) a port for receiving an assay device, said assay device comprising two or more capture regions; b) a reader comprising: i) one or more light sources for illuminating said two or more capture regions; ii) one or more light detectors for detecting optical signals from said two or more capture regions; and c) a data analyzer having one or more processors configured to: A) receive said optical signals; and B) determine an amount of at least a first analyte and a second analyte present in a biological sample based on said optical signals, wherein an optical signal of a first of said two or more capture regions increases with decreasing amounts of said first analyte present in said biological sample, and an optical signal of a second of said two or more capture regions increases with increasing amounts of said second analyte present in said biological sample. The diagnostic test system may include a housing for containing the components of the system. The housing can be constructed of any suitable material. The housing may be configured to receive an immunoassay device of the disclosure. For example, the housing may include a port or opening for receiving the immunoassay device. The cassette or housing of the immunoassay test device may include a cavity. The cavity, opening or port of the diagnostic test system may include a ball bearing contained within the inner wall of the chamber. The ball bearing may hook or latch into the cavity of the test device, thereby locking the immunoassay test device into the receiving chamber of the diagnostic test system. The system may further include, contained within the housing, a reader device. The reader device may include one or more light sources for illuminating the immunoassay device or a region of the immunoassay device. In one non-limiting example, the one or more light sources are configured to illuminate the capture zone of an immunoassay device of the disclosure. The type of light source suitable for use with the immunoassay devices will depend on the chemistry of the immunoassay device. In one particular example, the one or more light sources are used to illuminate a detectable label provided by the immunoassay device. In a particular example, the detectable label provided on the immunoassay device is a fluorophore, and therefore, the one or more light sources of the reader device should include a fluorescent light source (e.g., a light-emitting diode (LED)). It is to be understood that the wavelength of light provided by the light source of the reader device should be selected based on the excitation wavelength of the detectable label, and can readily be selected by a person of skill in the art. The reader may be configured to illuminate the capture zone and/or the control zone of an immunoassay device of the disclosure. For example, the reader may be configured to illuminate the first capture region, the second capture region, the first control region, the second control region, or any combination thereof. In some cases, the reader is configured to scan across the test strip of an immunoassay device. In such cases where the immunoassay device utilizes a single fluorophore, the reader may contain a single fluorescent light source. In cases where the immunoassay device utilizes more than one fluorophore, the reader may contain more than one fluorescent light source. The reader may further comprise one or more light detectors (e.g., a photodetector) for detecting optical signals from the immunoassay device. Generally speaking, the one or more light detectors should be capable of distinguishing between emitted light at a first discrete position and a second discrete position on the immunoassay device. This may be accomplished by, e.g., the one or more light sources scanning across the test strip of the immunoassay device and determining the position of the emitted light on the immunoassay device. The diagnostic test device may further comprise a data analyzer. The data analyzer may have one or more processors configured to receive an optical signal. In some cases, the data analyzer is in operable communication with a reader device. The data analyzer may be configured to determine an amount of analytes present in a sample, for example, by measuring an amount of optical signal produced at the capture zone of an immunoassay device. For example, the data analyzer may be configured to calculate the area under the curve of a signal intensity plot. The data analyzer may further be configured to determine the differences between signal intensities among the multiple discrete regions on the test strip. For example, the data analyzer may be configured to determine the difference between the signal intensity at the first capture region and the signal intensity at the second control region. The data analyzer may further be configured to determine the difference between the signal intensity at the second capture region and the signal intensity at the first control region. The data analyzer may further be configured to calculate an amount or concentration of the analytes present in the sample. The data analyzer may be further configured to detect a binary optical pattern. The binary optical pattern can be generated by two fluorescent materials which excitation and/or emission spectrum differs in wavelength. In some cases, the binary optical pattern can be generated by one fluorescent material and one light absorbent material. The detection reagents may be conjugated with the two types of materials respectively and can be captured in the same capture zone, such that the capture zone may generate two different optical signal patterns in the data analyzer. In some cases, the diagnostic test device, optionally in association with the data analyzer, generates measurement results (e.g., concentration or relative amounts of analytes present in the sample) from a completed assay performed on the test device, as described throughout. In some cases, the diagnostic test device displays the measurement results on the device screen. Data containing the measurement results can be transmitted from the diagnostic test device to a mobile device and/or to a server. The data may be transmitted via one or more wireless or wired communication channels. The wireless communication channels may comprise Bluetooth®, WiFi, 3G, and/or 4G networks.

An embodiment of the present invention comprises a testing system to detect the presence of PdG optimized for visual detection by a layperson's, or non-expert's, naked eye utilizing the embodiment in other than a laboratory context. The present inventor has recognized that in embodiments of the invention, the combination of mouse anti-PdG IgG1, IgG2a, IgG2b, and/or the IgG2c antibody conjugated to a visual label, such as colloidal gold and/or latex beads, and PdG conjugated to BGG carrier protein create sufficient binding partners. Resultantly, the preferred embodiment of the invention comprises a visual test readable by the untrained eye in a context outside of a laboratory environment, as depicted in FIGS. 4A-4B. In an embodiment, the visual label comprises colloidal gold 40 nm particles having an absorbance of 520-540 nm.

In varying embodiments of the invention, the visual label comprises particles having an absorbance of 380-750 nm which the present inventor notes is the approximate range typically perceptible to the human eye. In an alternative embodiment, the visual label comprises a fluorescent dye. In an embodiment, the fluorescent dye is readable only with the assistance of a machine configured to detect wavelengths on the visual spectrum outside of the range perceptible by the human eye. In an embodiment, the visual label comprises colloidal gold 40 nm particles having an absorbance of 520-540 nm.

As noted elsewhere in this application, the visual label in embodiments of the invention comprise particles having an absorbance of 380-750 nm which the present inventor notes is the approximate range typically perceptible to the human eye. In an alternative embodiment, the visual label comprises a fluorescent dye. In an embodiment, the configuration of the test strip and optionally a corresponding base unit are configured to allow for the interpretation of the results of the strip to indicate for the presence or absence of progesterone or analytes of progesterone due to the unique and novel configurations disclosed herein conjugated with a fluorescent label. An example of a lateral flow assay utilizing such a fluorescent dye label is described further in U.S. patent application Ser. No. 11/974,358, filed on Oct. 12, 2007, which is hereby incorporated by reference in its entirety. In an embodiment of the test strip, the visual label comprises particles having an absorbance of 190-380 nm, which the present inventor notes is the ultraviolet region imperceptible to the human eye. In an embodiment, the fluorescent dye is readable only with the assistance of a machine configured to detect wavelengths on the visual spectrum outside of the range perceptible by the human eye, which in an example is further described in U.S. patent application Ser. No. 11/974,358 mentioned above. The test results featuring a visual label imperceptible to the human eye of a test strip 3001 are optionally determinable by ultraviolet visible spectroscopy. In one embodiment, the device configured to interpret the results of a test strip featuring a visual label imperceptible to the human eye consists of a base unit 4001. In an alternative embodiment, the test results are interpreted with the assistance of a digital reader 3002. In an embodiment of the invention, the digital reader 3002 comprises a mobile phone device as depicted in FIG. 3.

The methods disclosed herein comprise one or more steps or actions for achieving the described method. The method steps and/or actions may be interchanged with one another without departing from the scope of the claims. The order and/or use of specific steps and/or actions may be modified without departing from the scope of the claims.

It is to be understood that the claims are not limited to the precise configuration and components illustrated above. Various modifications, changes and variations may be made in the arrangement, operation and details of the methods and apparatus described above without departing from the scope of the disclosure.

While the foregoing is directed to aspects of the present disclosure, other and further aspects of the disclosure may be devised without departing from the basic scope thereof.

I claim:

1. A single test comprising a lateral flow assay comprising both a sandwich assay and a competitive assay to detect for the presence or absence of at least PdG, the lateral flow assay configured to evaluate a non-serum bodily fluid, the lateral flow assay comprising:
   a sample pad;
   a first conjugate pad saturated with monoclonal anti-pregnanediol glucuronide (anti-PdG) antibodies of an isotype selected from the group consisting of IgG1, IgG1 Kappa, IgG2a, IgG2b, and IgG2c conjugated to a first visual label in a concentration of 1-10 ug/mL;
   a second conjugate pad saturated with antibodies selected from the group consisting of anti-luteinizing hormone, anti-follicle stimulating hormone, and anti-human chorionic gonadotropin, and conjugated to a second visual label;
   a membrane comprising a first testing zone and a second testing zone, the first testing zone comprising PdG conjugated to a globulin or Bovine Serum Albumin covalently linked to bind to PdG antigens at 8-32 molecules per carrier protein, and the second testing zone comprising an antibody selected from the group consisting of:
   anti-follicle stimulating hormone antibodies,
   anti-luteinizing hormone antibodies, and
   anti-human chorionic gonadotropin antibodies, to detect a hormone selected from the group consisting of:
   follicle stimulating hormone at a concentration of 1-30 mIU/ml, luteinizing hormone at a concentration of 1-50 mIU/ml, and
   human chorionic gonadotropin at a concentration of 1-10000 mIU/ml,
   the membrane providing a first observable result for the presence of PdG at or above a PdG threshold of 3-20 µg/ml as indicated by the absence of the color of the first visual label in the first testing zone following the operation of the lateral flow assay and the absence of PdG at or above a PdG threshold of 3-20 µg/ml as indicated by the presence of the color of the first visual label in the first testing zone following the operation of the lateral flow assay, and the membrane providing a second observable result for the presence of a hormone selected from the group consisting of follicle stimulating hormone, luteinizing hormone, and human chorionic gonadotropin, as indicated by the second visual label in the second testing zone following the operation of the lateral flow assay.

2. The single test of claim 1, the membrane further comprising a control line comprising antibodies reactive to the antibodies present in at least the first conjugate pad or the second conjugate pad.

3. The single test of claim 1, the first conjugate pad and the second conjugate pad together forming one singular combined conjugate pad, the singular combined conjugate pad saturated with monoclonal anti-pregnanediol glucuronide (anti-PdG) antibodies conjugated to a first visual label and additionally saturated with a conjugate or a plurality of conjugates comprising antibodies selected from the group consisting of anti-luteinizing hormone, anti-follicle stimulating hormone, and anti-human chorionic gonadotropin conjugated to a second visual label.

4. The single test of claim 1, the antibodies saturated on the first conjugate pad conjugated to a first visual label selected from the group consisting of colloidal gold, fluorescent dye and colored latex beads, and the antibodies saturated on the second conjugate pad conjugated to a second visual label selected from the group consisting of colloidal gold, fluorescent dye and colored latex beads.

5. The single test of claim 1, the first conjugate pad or the second conjugate pad further saturated with antibodies directed to an estrogen metabolite conjugated to a visual label, and the membrane further comprising a third testing zone to detect an estrogen metabolite at a concentration threshold of 1-1000 ng/ml, the third testing zone providing a third observable result for the presence or absence of an estrogen metabolite as indicated by the visual label in the third testing zone following the operation of the lateral flow assay.

* * * * *